United States Patent
Bake et al.

(10) Patent No.: US 9,439,678 B2
(45) Date of Patent: Sep. 13, 2016

(54) GUIDE TOOL FOR CARTILAGE REPAIR

(75) Inventors: Nina Bake, Lindingö (SE); Janarne Wetterheim, Bankeryd (SE); Robert Axelsson, Gränna (SE); Martin Qvänstedt, Bankeryd (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 289 days.

(21) Appl. No.: 14/112,576

(22) PCT Filed: Apr. 20, 2012

(86) PCT No.: PCT/EP2012/057318
§ 371 (c)(1),
(2), (4) Date: Dec. 27, 2013

(87) PCT Pub. No.: WO2012/143531
PCT Pub. Date: Oct. 26, 2012

(65) Prior Publication Data
US 2014/0142643 A1    May 22, 2014

Related U.S. Application Data

(60) Provisional application No. 61/477,808, filed on Apr. 21, 2011.

(30) Foreign Application Priority Data

Apr. 21, 2011 (EP) ..................................... 11163405

(51) Int. Cl.
*A61F 2/46* (2006.01)
*A61B 17/56* (2006.01)
*A61B 17/17* (2006.01)

(52) U.S. Cl.
CPC ........... *A61B 17/56* (2013.01); *A61B 17/1764* (2013.01); *A61B 2017/568* (2013.01); *A61B 2034/105* (2016.02); *Y10T 29/49* (2015.01)

(58) Field of Classification Search
None
See application file for complete search history.

(56) References Cited

U.S. PATENT DOCUMENTS

2005/0137600 A1    6/2005 Jacobs et al.
2008/0262624 A1    10/2008 White et al.

(Continued)

FOREIGN PATENT DOCUMENTS

JP    2001-520911 A    11/2001
WO    WO-2006/060416 A2    6/2006
WO    WO-2009/108591 A1    9/2009

OTHER PUBLICATIONS

Notice of Rejection dated Oct. 28, 2014, issued in corresponding Japanese patent application No. 2014-505657 (5 pages).

(Continued)

*Primary Examiner* — Sameh Boles
(74) *Attorney, Agent, or Firm* — Drinker Biddle & Reath LLP

(57) ABSTRACT

A method of designing a guide tool for cartilage repair in an articulating surface of a joint, comprising the steps of:
  I. determining physical parameters for cartilage damage in a joint and generating design parameters for cartilage repair objects and their relative placement in a predetermined pattern, comprising:
  II. selecting repair objects to fit the individual cartilage damage site wherein the repair objects have:
  cross sectional areas adapted to fit the surface area of the cartilage damage site,
  lengths adapted to fit the selected joint and/or type of cartilage damage, and
  surfaces intended to align with the articular cartilage surface in the joint, based on the healthy surface contour curvature,
  III. determining, based on obtained image data, positions and angles of the selected cartilage repair objects, wherein the positions and angles are adapted so that the selected repair objects fit the individual cartilage damage site,
  IV. generating design parameters of the guide tool, for placement of the cartilage repair objects comprising the following steps of:
generating the design for an upper part and a lower part of a guide channel in a guide body extending from the positioning body, said guide channel passing through said positioning body and said guide body wherein the angles and positions are generated dependent on and substantially corresponding to the determined angles and positions of the selected cartilage repair objects, and
wherein the design for the lower part of all the guide channel is generated dependent on and substantially corresponding to the determined cross sectional areas, of the selected cartilage repair objects.

15 Claims, 15 Drawing Sheets

(56) References Cited

U.S. PATENT DOCUMENTS

2009/0024131 A1  1/2009 Metzger et al.
2009/0209962 A1  8/2009 Jamali
2009/0221898 A1  9/2009 Hillis et al.
2010/0121389 A1  5/2010 Librot et al.
2010/0292704 A1  11/2010 Stoffel et al.

OTHER PUBLICATIONS

Office Communication dated Jun. 25, 2015, issued in corresponding European patent application No. 12 714 736.1 (7 pages).

Notice of Rejection dated Jun. 23, 2015, issued in corresponding Japanese patent application No. 2014-505657 (with English translation) (4 pages).

GUIDE TOOL FOR CARTILAGE REPAIR

CROSS-REFERENCE TO PRIOR APPLICATIONS

This application is a §371 National Stage Application of PCT International Application No. PCT/EP2012/057318 filed Apr. 20, 2012, which claims priority to European Patent Application No. 11163405.1 filed Apr. 21, 2011 and U.S. Provisional No. 61/477,808 filed Apr. 21, 2011, each of which are herein incorporated by reference in their entirety.

FIELD OF THE INVENTION

This invention relates in general to the field of orthopedic surgery and to surgery tools. More particularly the present invention relates to a surgery guide tool, which may be comprised in a kit comprising a kit of tools for replacement of damaged cartilage at an articular surface in a joint such as a knee, ankle, hip, shoulder, elbow, fingers and foot.

BACKGROUND

General Background

Pain and overuse disorders of the joints of the body is a common problem. For instance, one of the most important joints which are liable to wearing and disease is the knee. The knee provides support and mobility and is the largest and strongest joint in the body. Pain in the knee can be caused by for example injury, arthritis or infection. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibro cartilage. This means that damages of the cartilage gradually become worse. Along with injury/disease comes a problem with pain, which results in handicap and loss of function. It is therefore important to have efficient means and methods for repairing damaged cartilage in knee joints.

Today's knee prostheses are successful in relieving pain but there is a limit in the lifetime of the prostheses of 10-15 years. The surgical operation is demanding and the convalescence time is often around 6-12 months. In many cases today, surgery is avoided if training and painkillers can reduce the pain. Prostheses are therefore foremost for elderly patients in great pain, at the end of the disease process; a totally destroyed joint. There are different kinds of prostheses, such as half prosthesis, total prosthesis and revision knee, the latter used after a prosthesis failure. The materials used in today's knee prostheses are often a combination of a metal and a polymeric material, but other materials such as ceramics have also been used. The size of knee prostheses makes it necessary to insert them through open surgery.

All treatments have shown only limited results, with implications such as high cost, risk of infection, risk of loosening, limited suitability for patients of different ages and the extent and location of damage.

SPECIFIC BACKGROUND

Other attempts, except using prostheses, practiced at various clinics around the world with the main objective to repair or rebuild cartilage include biological approaches such as micro fractures, cartilage cell transplantation (ACI), periost flap, and mosaicplasty surgery.

In the surgical operation of repairing cartilage tissue using transplants or implants it is critical that the cartilage repair object, for example an implant or a transplant, for example a healthy cartilage and bone plug is positioned in a precise manner. If the cartilage repair object is offset from its intended position it may cause increased wear or load on the joint. For example, if the cartilage repair object is tilted this may result in an edge that projects above the cartilage surface and causes wear on the opposing cartilage in the joint. Another example is when the cartilage repair object is placed in a position with the surface of the cartilage repair object projecting above the surface of the cartilage causing the joint to articulate in an uneven manner and increasing the load on an opposing point of the joint. For the patient, also small misplacements or deviations from an ideal position may result in pain, longer time for convalescence or even a surgical operation being done in vain and making it more difficult to repair the damage in the joint. Today there are known guide tools which may assist during placements of single implants or single transplants.

Implantation of healthy cartilage and bone plugs into damaged cartilage areas is especially advantageous for young patients which still are growing and which has better abilities for self repair of cartilage compared to adults. Mosaicplasty involves moving round 'plugs' of cartilage and underlying bone to damaged areas. The plugs are each a few millimeters in diameter, and when multiple plugs are moved into a damaged area the result is a mosaic appearance. The multiple small plugs of cartilage look like mosaic tiles. Osteochondral autograft transfer (OATS) is a technique very similar to mosaicplasty but during OATS procedure the plugs are usually larger, and therefore only one or two plugs are needed to fill the area of cartilage damage. Because of this it does not take on the mosaic appearance, but the principle is the same.

Today mosaicplasty or osteochondral autograft transfer (OATS) is performed using a graft harvesting tool, which harvests the osteochondral plug in a desired size. After the osteochondral plug is collected the plug is then placed in the recipient hole by using a plunger which is a part of the harvesting tool. These tools are not easy to use and a large burden is therefore placed on the surgeon in order not to misplace or misfit the implant.

Supported grafts heal well, but unsupported grafts tend to subside and become covered by fibrous tissue. It is therefore important that the implanted plugs are correctly sized and the graft is seated in a well-supported recipient site.

The guide tools on the market are lacking supportive design which gives a reliable, repeatable, cartilage repair with exact preciseness during placement of the implants. The implants on the market today is relying on the skills of the surgeon.

PRIOR ART

Examples of prior art disclosing tools for replacement of damaged cartilage using mosaic plasty or osteochondral autograft transfer (OATS) or other methods where the damaged cartilage and bone are replaced with healthy cartilage and bone are described in the following documents:

WO 2009/108591 A1 describes a method of repairing an articular cartilage defect including use of a drill guide guiding drill holes in different angles into the bone.

US2009/0209962 A1 describes a device and a technique for preparation and implantation of osteochondral allografts for resurfacing of a human joint. The technique involves use of a guide comprising an inner guide and an outer guide wherein the articular surface of the guide matches the articular surface of both the allograft and the recipient bone. The guide may be manufactured using computer technology and rapid prototyping. The outer guide is secured with guide pins to the allograft site.

US20100292704 A1 describes an implant inserter device comprising a pushrod slidable received within an outer collar of the device, which may be used to place an implant in a damaged cartilage area. A guide wire is used to guide a lesion gauge (mounted on the guide wire) in position for removal of damaged cartilage and bone.

US2005/0137600 A1 describes a technique and instruments for repair of articulate cartilage in joints. For example an implant delivery device, which functions both as a cartilage cutter and a guide and which comprises a push rod.

WO2006/060416 A2 describes devices and a method for cartilage repair wherein the devices comprise a drill guide having a proximal end shaped and conformed to the shape of the tissue at the perimeter of the defect.

US 2009/024131 A1 describes a device for an orthopedic knee procedure. The device can include a drill guide. The device includes two guides, an alignment guide with a body with an inner anatomically-engaging surface shaped to closely conform and mate with a corresponding tibia joint surface and a drill guide wherein the alignment guide is mounted on the tibial joint surface and the drill guide is mounted on the alignment guide. The guides are made from a pre-operative plan formed from an MRI or CT scan of the patient and rely on matching subcutaneous anatomic feature for correct positioning. The guide described is not intended for small cartilage damage repair or for guiding placement of implants. It is a guide for drilling before fastening larger implants.

US 2010/121389 A1 describes A method of preparing a distal femur to implantation of a femoral implant. The surgeon then evaluates whether the holes in the femur are located appropriately to securely implant the femoral implant onto the femur. This guide does not guide the placement of small cartilage repair implants instead it guides the drilling of holes for placement of larger implants.

US 2008/262624 A1 describes an implant which has a first portion including at least one patient-adjustable feature and a second portion including at least one standard feature. This implant allows for standard cutting guides to be used for implantation.

US 2009/221898 A1 describes a method for making a customized medical device based on a patient image using a rapid prototyping machine. The guide is a customized cutting block and not a guide for guiding small implants.

The solutions described in the prior art above to a great extent destroys more of the original cartilage in a patient than necessary.

OBJECT OF THE INVENTION

General Object

The general object of the invention is to provide means for enabling precision of the insertion and positioning of the cartilage and bone plugs or implants at an articular surface of a joint. The invention further solves the problem of providing tools, for example individually customized tools which enables guiding of other insert tools when making cartilage and bone plugs comprising healthy cartilage during mosaicplasty or osteochondral autograft transfer (OATS) or enables guiding of implants.

Partial Problems

The invention further seeks to solve the partial problems of:

Providing a well fitting cartilage repair object from a non bearing area of a joint.

Providing a method of insertion of a cartilage repair object in the damaged bearing area of the joint and is well integrated into the surface structure of the joint, in order to generate optimal repair of damaged tissue and wherein the method causes minimum damage to the surrounding tissue.

Providing a method for picking and choosing plugs or implants of appropriate top curvature, depth and angle and also method for placing such plugs or implants Providing means for implanting cartilage repair objects into the joint for example plugs or implants, improving the positioning of the cartilage repair object in order to generate optimal repair of damaged tissue and cause minimum damage to the surrounding tissue and aiding the surgeon in that positioning.

Providing a design method for a guide tool used during cartilage repair in a joint, for example during cartilage repair of small cartilage damages, where precision is important and where a part or a small portion of the cartilage in the joint is replaced with plugs or implants.

SUMMARY OF THE INVENTION

The present invention provides a method for replacing a portion, e.g. diseased area and/or area slightly larger than the diseased area, of a joint, e.g. cartilage and/or bone, with a cartilage repair object and a guide tool which achieves a near anatomic fit of the cartilage repair object with the surrounding structures and tissues.

A first aspect of the invention is a guide tool for cartilage repair at an articulating surface of a joint used to guide harvesting and also insertion of a healthy cartilage and bone plug from a non bearing part of a joint to an area replacing the cartilage of a cartilage injury site. The guide tool according to the invention may also be used to guide insertion of implants. The actual harvesting may be performed using a cartilage harvesting tool inside the guide tool according to the invention. The individually designed guide tool according to the invention may be designed to harvest plugs or designed for placement of plugs into the damage site or designed to be able to guide both harvesting and placement of plugs or implants. The cartilage harvesting tool used inside the guide tool may also be equipped with a plunger used for the placement of the harvested cartilage and bone plug into the damaged cartilage area.

The guide tool is equipped with a positioning body and a guide body with at least one guide channel which goes through said positioning body and said guide body. The positioning body has a cartilage contact surface that is designed to fit the contour of the cartilage or subchondral bone in the joint in a predetermined area surrounding the site of diseased cartilage. The positioning body has a guide channel which has at least one cross-sectional profile that is designed to correspond to an insert tool. The guide channel has at least one muzzle facing the cartilage surface at a position corresponding to the site of the diseased cartilage.

The insert tools are used inside the guide channel of the guide tool. The insert tools may fit in the guide channel, with a slight tolerance to allow a sliding movement of the cartilage harvesting and the insert tool into the guide channel. The insert tools are in different embodiments of the invention provided e.g. as a cartilage harvesting and insert tool or as a drill bit.

A guide tool according to the invention is equipped with a positioning body comprising a guide body comprising at least one or more guide channels and a cartilage contact surface and wherein the cartilage contact surface is designed to fit the individual contour of the cartilage or subchondral bone in the joint in a predetermined area surrounding a site of diseased cartilage and said guide channels have a cross-sectional profile that is designed to correspond to a cross-section of the insert tools and each guide channel has a muzzle facing a cartilage damage at a position facing the site of the diseased cartilage, characterized in that the guide channels are placed or designed for placement within the guide body in a predetermined pattern, wherein the position and relative distance and angle of said guide channels are designed to fit an individual cartilage damage site.

In another embodiment the guide tool 1 according to the invention has at least one of said guide channels 200 having an outer portion 234 and an inner portion 232 and that said outer portion 234 is larger in volume than said inner portion 232 and between the outer portion 234 and the inner portion 232 is a stop function 214 or the cross-sectional diameter 212 of the outer portion 234 is smaller than the cross-sectional diameter 262 of the inner portion 232 or for example the cross-sectional diameter 212 of the outer portion 234 is less than 30% smaller or 1-20% smaller compared to cross-sectional diameter 262 of the inner portion 232.

In another embodiment a guide tool 1 according to the invention has a cartilage contact surface (208) of the positioning body 206 of the guide tool 1 having three contacting points, spread out around the guide body 206, for contacting parts of the joint in order to provide stable positioning of the guide tool 1 in the joint.

In another embodiment a guide tools according to the invention has a cartilage contact surface 208 located on the positioning body 206 of the guide tool 1 and the cartilage contact surface 208 has three contacting points, spread out around the guide body 206, for contacting parts of the joint in order to provide stable positioning of the guide tool 1 in the joint. For example the cartilage contact surface may be 10-90% larger than the area of the muzzle or the cartilage contact area may be perforated in 10-90 area % by muzzle openings.

The guide tool (1) according to the invention comprises a guide channel (200) and a positioning body (206) which further comprises a cartilage contact surface (208). The positioning body (206) extends laterally outside the periphery of the guide channel (200)

In another embodiment a guide tool 1 according to the invention, has a guide channel 200 having a height 218 of 0.3-20 cm or preferably 3-10 cm.

In another embodiment the repair system according to the invention, includes cartilage repair objects which are implants or a healthy cartilage and bone plugs.

In another embodiment a guide tool 1 according to the invention has a relative shortest distances 804 between the guide channels of 1-3 mm.

In another embodiment a guide tool 1 according to the invention comprises guide channels with a relative shortest distances 804 between the guide channels of 1-3 mm.

In another embodiment, the method of designing a guide tool 1 for cartilage repair in an articulating surface of a joint according to the invention, comprises the steps of:

I. determining physical parameters for cartilage damage in a joint and generating design parameters for cartilage repair objects 600 and their relative placement in a predetermined pattern, comprising:
  a. selecting repair objects to fit the individual cartilage damage site wherein the repair objects have;
    cross sectional areas adapted to fit the surface area of the cartilage damage site
    lengths adapted to fit the selected joint and/or type of cartilage damage
    surfaces intended to align with the articular cartilage surface in the joint, based on the healthy surface contour curvature
  b. determining, based on the obtained image data, positions and angles of the selected cartilage repair objects, wherein the positions and angles are adapted so that the selected repair objects fit the individual cartilage damage site
II. generating design parameters of the guide tools, for placement of the cartilage repair objects comprising the following steps;
  a) generating the design for an upper part 234 and a lower part 232 of a guide channel 200 in a guide body 206 extending from the positioning body 202, said guide channel 200 passing through said positioning body 202 and said guide body 206 wherein the angles and positions are generated dependent on and substantially corresponding to the determined angles and positions of the selected cartilage repair objects, and wherein;
    the design for the lower part 232 of all the guide channel 200 is generated dependent on and substantially corresponding to the determined cross sectional areas, of the selected cartilage repair objects.

In another embodiment, the method of designing a guide tool 1 for cartilage repair in an articulating surface of a joint according to the invention, comprises the steps of: determining physical parameters for a cartilage damage in a joint and generating design parameters for a number of cartilage repair objects 600, size of cartilage repair objects 600 and their relative placement in relation to the other cartilage repair objects in a predetermined pattern depending on the cartilage damage, comprising:

2. selecting cartilage repair objects 600 to fit the individual cartilage damage site in a joint wherein said repair objects have;
  cross sectional areas adapted to fit the surface area of the cartilage damage site, in combination with other cross section areas of other repair objects or alone
  lengths adapted to fit the selected joint and/or type of cartilage damage
  surfaces intended to align with the articular cartilage surface in the joint, based on the healthy surface contour curvature
3. determining, based on the obtained image data received from X-ray, CT, MRI or other imaging techniques scanning the cartilage damage in a patient, positions and angles of the selected cartilage repair objects, wherein the positions and angles are adapted so that the selected repair objects fit said individual cartilage damage site
4. generating design parameters of the guide tool 1, designed for placement of the cartilage repair objects comprising the following steps;
  a) generating the design for an upper part 234 and a lower part 232 of a guide channel 200 in a guide body 206 extending from the positioning body 202, said guide channel 200 passing through said positioning body 202 and said guide body 206 wherein the angles and positions are generated dependent on and substantially corresponding to the determined angles and positions of the selected cartilage repair objects, and their intended or designed placement in a joint wherein;

the design for the lower part 232 of all the guide channel 200 is generated dependent on and substantially corresponding to the determined cross sectional areas, of the selected cartilage repair objects.

b)

In another embodiment the method of designing a guide tool (i) for cartilage repair in an articulating surface of a joint according to the invention comprises the steps of:

I. determining physical parameters for cartilage damage in a joint and generating design parameters for cartilage repair objects (600) and their relative placement in a predetermined pattern, comprising:
   a) obtaining image data representing a three dimensional image of a bone member of the joint;
   b) identifying in the obtained image data and individual cartilage damage in an articulate surface of the bone member;
   c) determining based on the obtained image data the location of the individual cartilage damage;
   d) determining based on the obtained image data the size and shape of the individual cartilage damage;
   e) determining a cartilage damage site based on the determined size and shape of the cartilage damage;
   f) determining based on the obtained image data the surface contour curvature of the individual cartilage damage site 92 and/or the subchondral bone in the joint in the predetermined area comprising the individual cartilage damage site;
   g) determining a representation of a healthy surface contour curvature comprising the individual cartilage damage site
   h) selecting repair objects to fit the individual cartilage damage site wherein the repair objects have;
      cross sectional areas adapted to fit the surface area of the cartilage damage site
      lengths adapted to fit the selected joint and/or type of cartilage damage
      surfaces intended to align with the articular cartilage surface in the joint, based on the healthy surface contour curvature
   i) determining, based on the obtained image data, positions and angles of the selected cartilage repair objects, wherein the positions and angles are adapted so that the selected repair objects fit the individual cartilage damage site II. generating design parameters of the guide tool 1, for placement of the cartilage repair objects comprising the following steps;
   a. generating the contact points for a cartilage contact surface 208 of a positioning body 202 dependent on said determined surface contour curvature of the cartilage and/or the subchondral bone in the joint in a predetermined area comprising and surrounding the site of cartilage damage, such that said cartilage contact surface 208 of the positioning body 202 fits to said surface contour of the cartilage or the subchondral bone in the joint.
   b. generating the design for an upper part 234 and a lower part 232 of a guide channel 200 in a guide body 206 extending from the positioning body 202, said guide channel 200 passing through said positioning body 202 and said guide body 206 wherein the angles and positions are generated dependent on and substantially corresponding to the determined angles and positions of the selected cartilage repair objects, and wherein;
      the design for the lower part 232 of all the guide channel 200 is generated dependent on and substantially corresponding to the determined cross sectional areas, of the selected cartilage repair objects 600
   c. Optionally generation of suggestions of where and how the healthy cartilage and bone plug are to be harvested in a manner so that the contour curvature for the articulate surface of the bone plug corresponds to the curvature that covers the cartilage damage wherein the cartilage and bone plug are to be placed.

In another embodiment the method of designing a guide tool 1 for cartilage repair in an articulating surface of a joint according to the invention, includes generating design parameters for the guide channel 200 to have a height 218 of 0.3-20 cm for example of 3-10 cm.

In another embodiment the method of designing a guide tool 1 for cartilage repair in an articulating surface of a joint according to the invention includes a cartilage repair object which is an implant or a healthy cartilage and bone plug.

In another embodiment the method of designing a guide tool 1 for cartilage repair in an articulating surface of a joint according to the invention includes image data representing an image of the joint is obtained using magnetic resonance imaging (MRI), computerized tomography (CT) imaging or a combination of both, or other suitable techniques such as delayed Gadolinium-enhanced MRI of cartilage (dGEMRIC) techniques.

In another embodiment the guide tool is designed to replace a small cartilage damage only replacing a part of the cartilage in a joint. For example using cartilage repair objects with crossectional profiles of between 0.1 $cm^2$ and 5 $cm^2$, between 0.5 $cm^2$ and 3 $cm^2$, or preferably between about 0.5 $cm^2$ and 2 $cm^2$ intended to repair cartilage damages of areas between 0.1-10 $cm^2$.

In another embodiment the guide tool is designed to comprise at least one muzzle which in total has an area of 10-90% of the total cartilage surface area spread of the guide tool.

In another embodiment the guide tool is designed to comprise a design for the lower part 232 of all the guide channel 200 generated dependent on and substantially corresponding to the determined cross sectional areas, of the selected cartilage repair objects boo in order to make the guide tool suitable to guide the insertion of the cartilage repair objects into the cartilage repair site.

In another embodiment according to the invention the guide tool is designed to be suitable for preparing the cartilage damage site before placing of implants or plugs and also for guiding the placing cartilage repair objects into the cartilage repair site of a joint.

In another embodiment according to the invention the guide tool is designed to insert plugs or implants which has a diameter of between 0.1 $cm^2$ and 5 $cm^2$, between 0.5 $cm^2$ and 3 $cm^2$, or preferably between about 0.5 $cm^2$ and 2 $cm^2$.

In another embodiment according to the invention the guide tool is designed to have a muzzle with a cross sectional diameter which is determined depending on the size and shape of the crossectional diameter of the implants or bone plugs so that the muzzle of the guide tool corresponding to the crossectional diameter of the implants or bone plugs in a way that the implants or bone plugs allows to be inserted through the muzzle. For example the cross-sectional area of the muzzle is designed to differ in +/−0-5% compared to the crossectional area of the implants or plugs.

Further a method using the guide tool 1 according to the invention comprises the steps;
- a) using the data and the guide tool designed according to the design method described in claims 6-9
- b) inserting the individually shaped guide tool from step a) on the cartilage damage site 806 and optionally fastening the guide tool to the cartilage.
- c) using selected guide channels 200 in the guide tool 1 for guidance when drilling out recesses in the bone and cartilage within the cartilage damage site of the patient.
- d) placing selected cartilage repair objects 600 into recesses created in step c) using the guide tool 1 for guidance.

BRIEF DESCRIPTION OF THE FIGURES

The present invention will be further explained below with reference to the accompanying drawings, in which.

DETAILED DESCRIPTION OF THE INVENTION

Introduction

Figure 1:
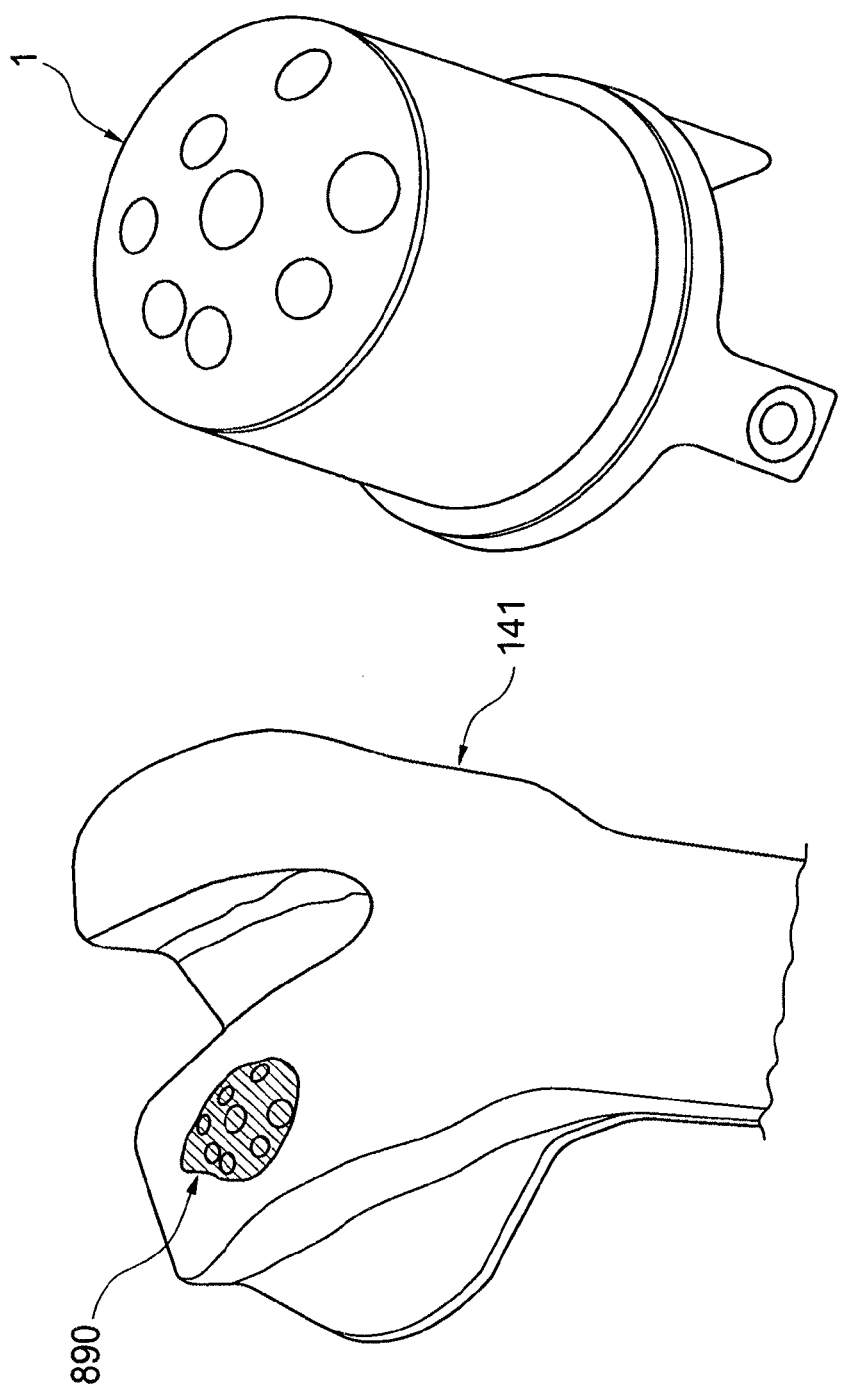
FIG. 1 shows an exemplifying embodiment of a knee joint with a cartilage repair site repaired using the cartilage repair system according to the invention and a guide tool.

This invention concerns a guide tool for use in orthopedic surgery more precisely during mosaicplasty or osteochondral autograft transfer (OATS) or during implantation of implants, FIG. 1 shows a representation of a femoral bone 141 with a cartilage repair site 890 made according to the method of the invention and using a guide tool 1 according to the invention. The guide tool according to the invention guides the use of surgical tools used during a cartilage repair surgery. The surgical tools or insert tools may be used inside the guide tool and thereby supported by the guide tool during surgery. Further the guide tool guides insertion of the implants or plugs into the cartilage damage.

Typical cartilages damages intended to be repaired using the guide tool according to the invention are damages in which only a small part of the joint is damaged. For example to repair cartilage damages of 1-5 cm$^2$ or 1-2 cm$^2$ 0-1 cm$^2$ or for example cartilage damages of 1-70%% of a cartilage surface in a joint.

The guide tool may guide preparation of the cartilage damage site in a joint before placement of cartilage repair object into the damaged insert site. A cartilage repair object may for example be a healthy cartilage and bone plug or an implant. Preparation of the cartilage repair object site may for example be done using a drill bit which is guided, by the guide tool to make recesses in certain angles into the bone at the site for the cartilage damage. The prepared recesses in the bone are used for the placement of cartilage repair objects.

The guide tool is for example designed to comprise guide channels which has predetermined angles and location and sized depending on the cartilage damage.

Figure 3:
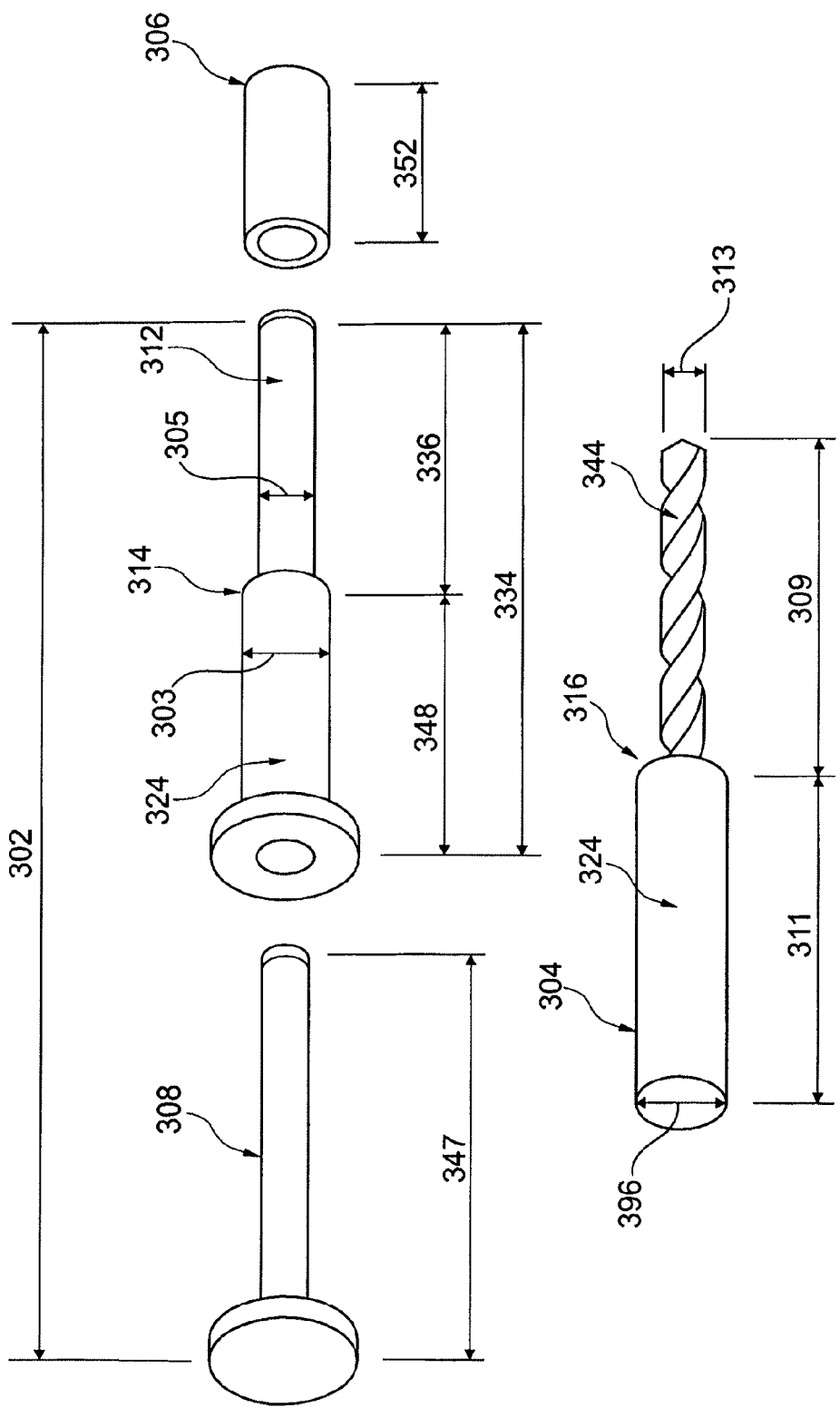
FIG. 3 shows an exemplifying embodiment of different insert tools which may be used inside the guide channels of the guide tool; cartilage harvesting and insert tool and a drill tool according to the present invention.

A guide tool according to the invention may be used together with different insert tools for example a cartilage harvesting and insert tool 302 in FIG. 3 for guiding the placement of healthy cartilage plugs replacing damaged cartilage in a joint. The guide tool according to the invention may also be used together with other inserts tools for example tools guiding the harvesting of healthy cartilage plugs from a non bearing part of a joint to a prepared site.

Figure 13:
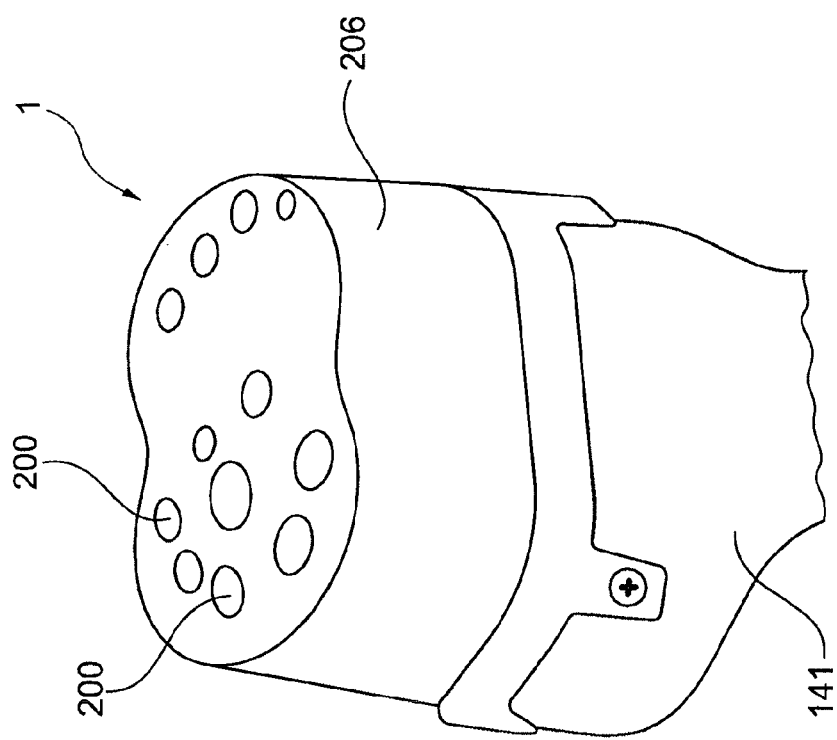
FIG. 13 shows an exemplifying embodiment of the invention, wherein the guide tool covers both the harvesting cartilage area and the cartilage area of the cartilage damage.

In one exemplified embodiment of the invention, see FIG. 13, the guide tool covers both the harvesting area and the cartilage area of the cartilage damage having some guide channels designed and adapted for guiding tools for harvesting cartilage repair object from a non bearing part of a knee and other guide channels designed for guiding insert tools used for insertion of cartilage repair objects into the prepared recesses or guiding tools used for drilling recesses.

Figure 14:
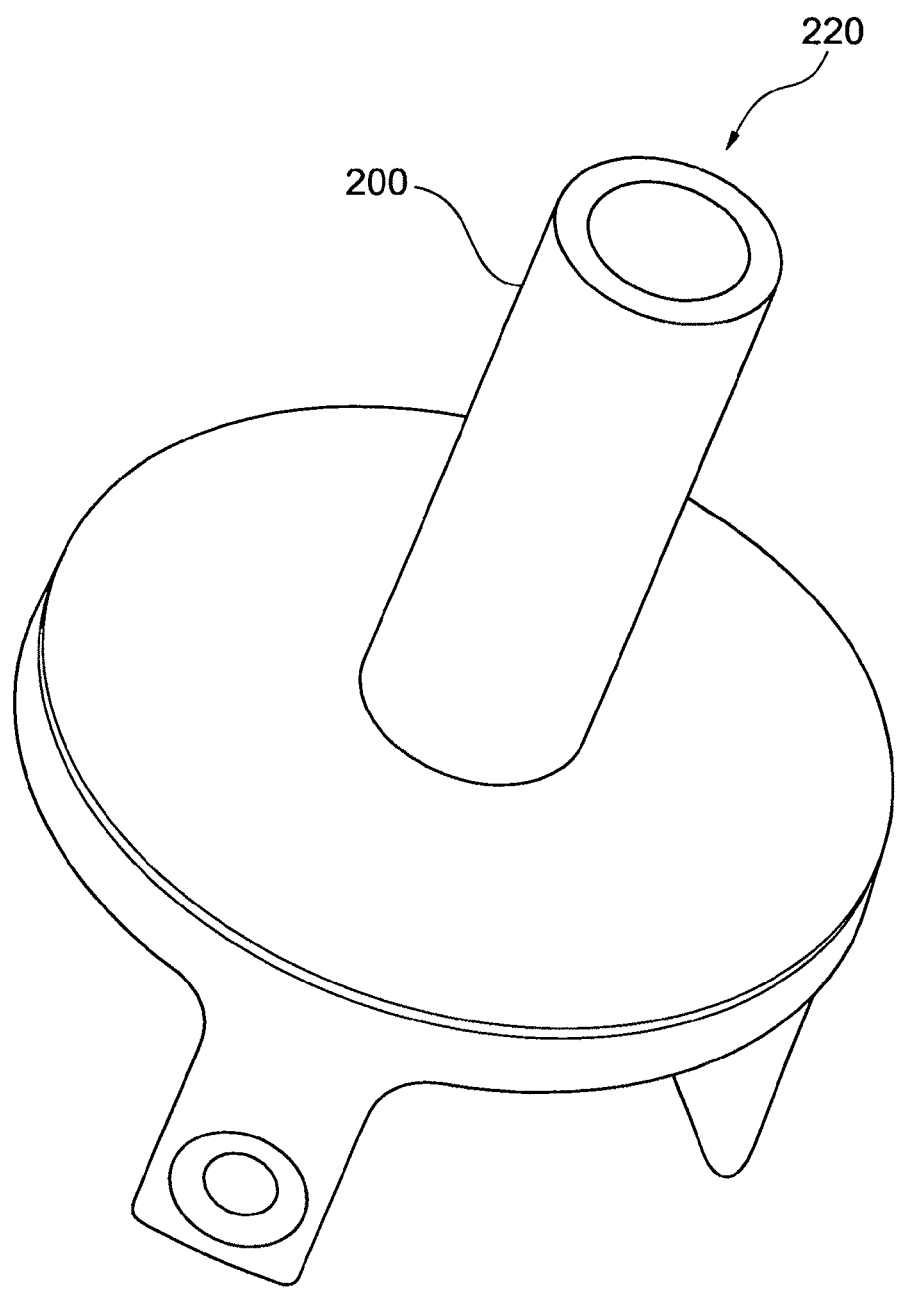
FIG. 14 shows an exemplifying embodiment of the invention, wherein the guide tool comprises one guide channel

In another exemplified embodiment of the invention, see FIG. 14, the guide tool comprises one guide channel.

Figure 15:
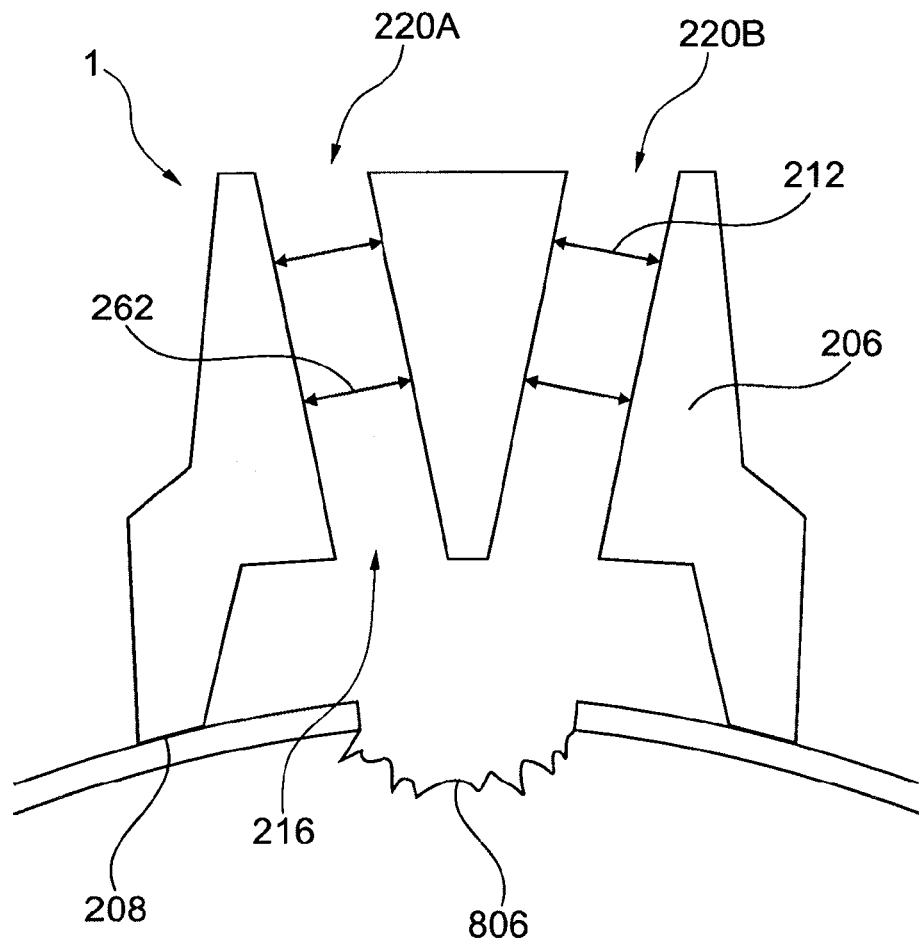
FIG. 15 shows an exemplifying embodiment of the invention, wherein the guide tool comprises guide channels having a lower and an upper part with the same diameter.

In further an exemplified embodiment the guide tool according to the invention is designed to comprise a guide tool with guide channels where the upper body 324 with a diameter 396 and a lower body 344 with a diameter 313 wherein the diameter 396 and the diameter 313 is of the same size, see FIG. 15.

The present invention also provides a method for replacing a portion, e.g. diseased area and/or area slightly larger than disease area, of a joint, e.g. cartilage and/or bone, with an cartilage repair object using a guide tool which enables the surgeon to place the cartilage repair objects in a near anatomic fit of the repair objects with the surrounding structures and tissues. For example the size of the cartilage damage is 1-70% of the total cartilage in the joint to be repaired. The guide tool according to the invention is designed to repair cartilage damages of a size of the cartilage damage is 1-70% of the total cartilage in the joint with high precision.

A first aspect of the invention is a guide tool used for guiding insert tools during cartilage repair at an articulating surface of a joint. The guide tool may be designed allowing cartilage repair objects to be harvested in a non bearing part of the joint and at the same time allowing placement of the cartilage repair objects in the damaged site in the joint. The guide tool may for example be designed to comprise at least one guide channel designed to harvest at least one cartilage repair objects and also at least one other guide channel designed to place cartilage repair objects.

Figure 2:
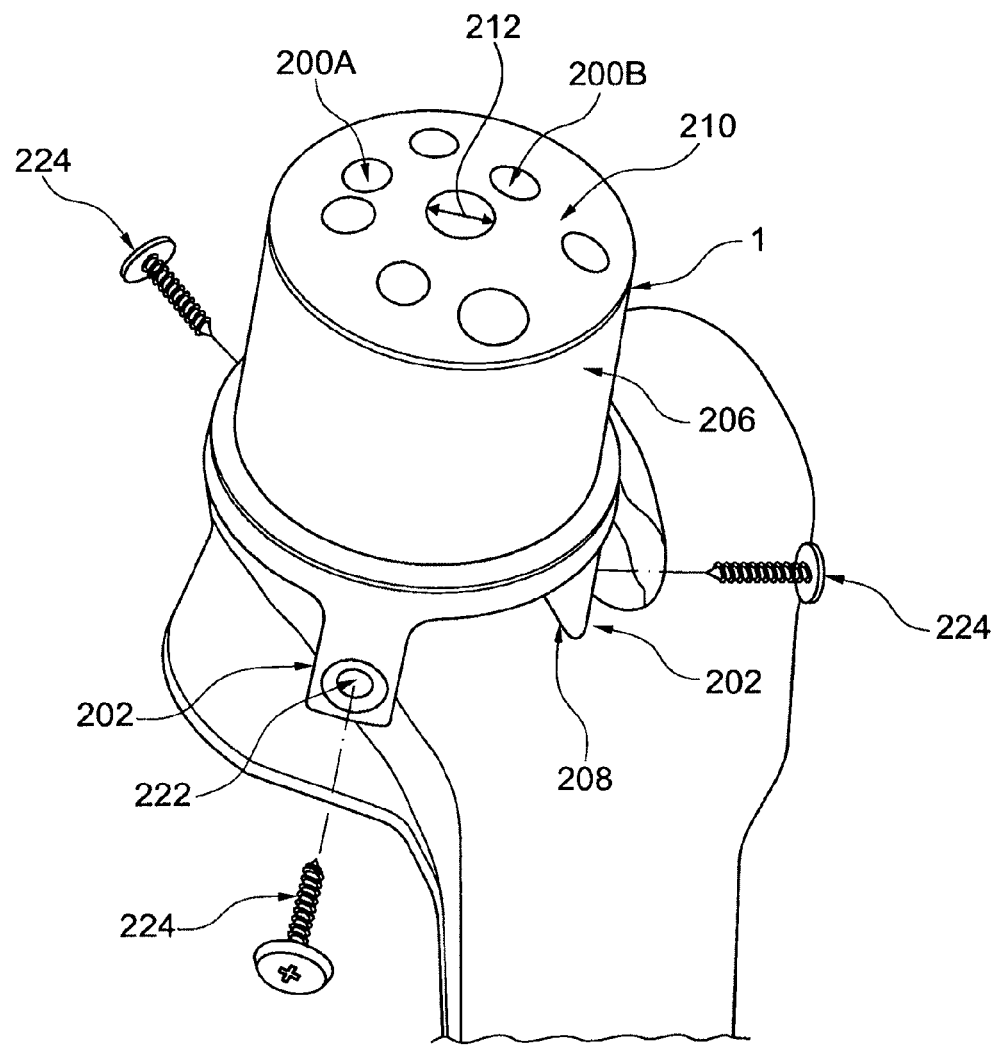
FIG. 2 shows an exemplifying embodiment of a guide tool according to the present invention placed in a knee joint.

The guide tool 1 according to the invention, see FIG. 2 for an exemplified embodiment, is equipped with a positioning body 202 comprising a cartilage contact surface 208 and a guide body 206. The guide body 206 has a top surface 210 and comprises at least two guide channels 200 having a cross sectional diameter 212. The guide channels 200 are designed to fit insert tools used inside the guide tool 1, for example a plug harvesting and/or insertion tool. For example the guide channels 200 are designed to fit the insert tools so that the insert tools may glide with a precise fit inside the guide channel allowing precise guidance of the guide tool.

The guide tool 1 may also be used to guide other surgical tools or insert tools within the guide channels 200 of the guide tool 1. The guide tool 1 may guide harvesting and/or also insertion of a healthy cartilage and bone plug/s from a non bearing part of a joint or insertion of implants to an area replacing the cartilage of a cartilage injury site.

In FIG. 2 rivets 224 are also shown that can be used to fasten the guide tool 1 to the bone in using the drill holes 222 placed in the positioning body 202 of the guide tool 1.

Examples of insert tools can be seen in FIG. 3. The insert tools may for example be a cartilage harvesting and insert tool 302 or a drill bit 304.

The cartilage harvesting and insert tool 302 may comprise of different parts, for example a plunger 308, which has a length 347 of for example 3-40 cm, a hollow body, which has a length 347 of 3-20 cm and which comprises an upper part 324, which has a diameter 303 and a length 348 and a lower part 312, which has a diameter 305 and a length 336. Between the upper part 324 and the lower part 312 is a stop function 314. The diameter 303 (for example 0.2-1 cm) of the upper part 324 is larger than the diameter 305 (for example 0.1-0.9 cm) of the lower part 314 of the cartilage harvesting and insert tool 302. Further the cartilage harvesting and insert tool 302 may comprise a depth control function 306 which has a length 352 of for example 1-2 cm.

The drill bit 304 comprises of an upper body 324 with a diameter 396 (for example 0.1-5 cm or 0.2-1 cm) and a length 311 and a lower body 344 with a diameter 313 (for example 0.1-5 cm or 0.1-0.9 cm) and a length 309. Between the upper body 311 and the lower body 312 is a stop function 316.

Harvesting of fresh cartilage plugs from a non bearing part of a joint is performed using insert tools inside the guide tool 1 such as using a cartilage harvesting and insert tool 302 inside the guide tool 1, see FIG. 3. The cartilage harvesting and insert tool 302 may also be equipped with a plunger 308 used for placement of the harvested cartilage and bone plug into the damaged cartilage area. In another embodiment the plug harvesting tool and the inserting tool are two different tools both used inside the guide tool 1 for appropriate guidance when harvesting or inserting the cartilage plug into or from the bone.

Figure 4:
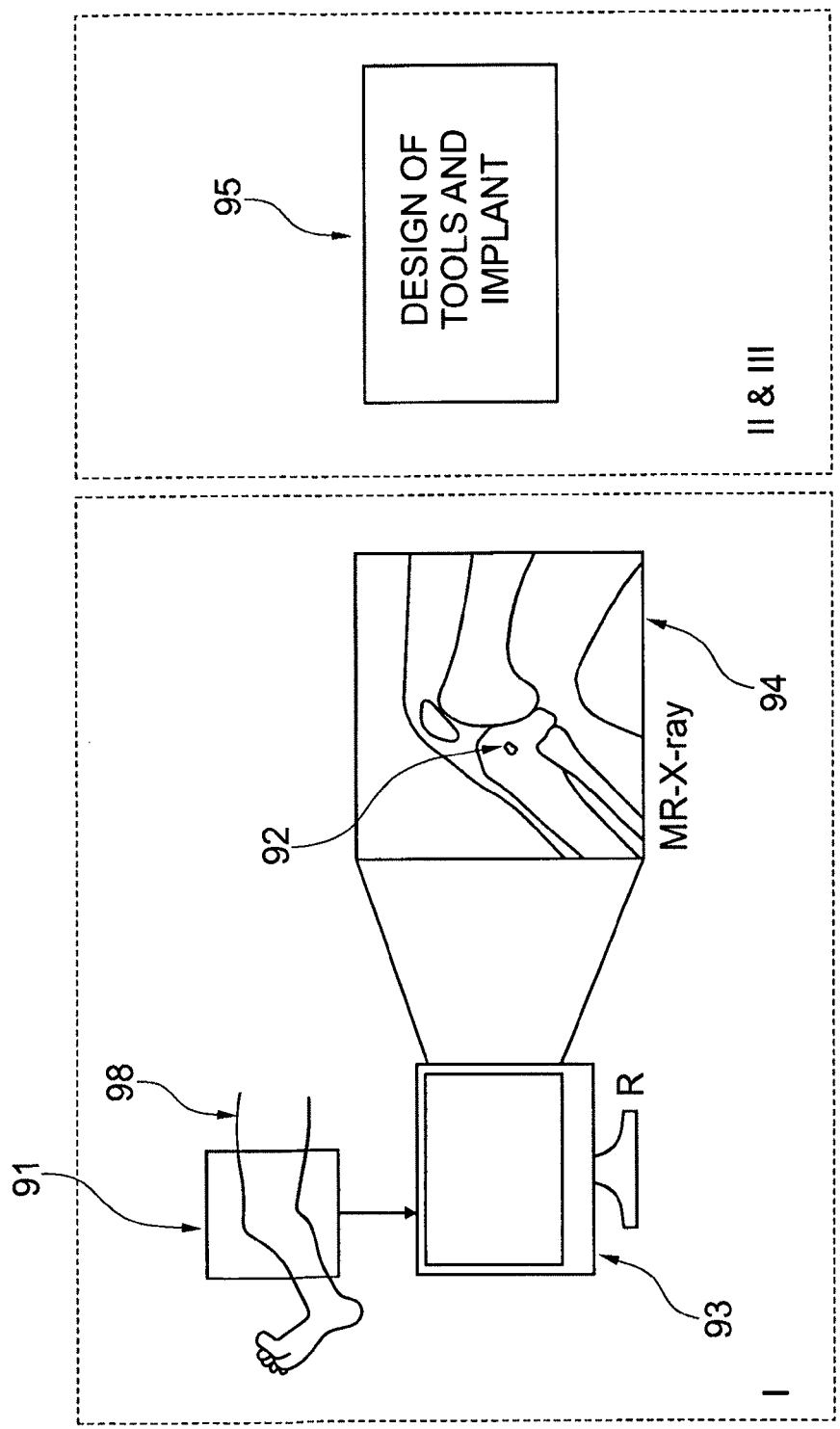
FIG. 4 shows a schematic overview of an exemplifying embodiment of a design method in accordance with the invention used for designing a patient specific guide tool.

The guide tool 1 is designed using a design or CT system, see FIG. 4, wherein a knee with the cartilage damage 92 is examined using MR-X-ray 91 and analyzed and processed in a computer 93 and wherein the collected data 94 is further processed and used in the design 95 of the guide tool 1.

The Guide Tool

Figure 5:
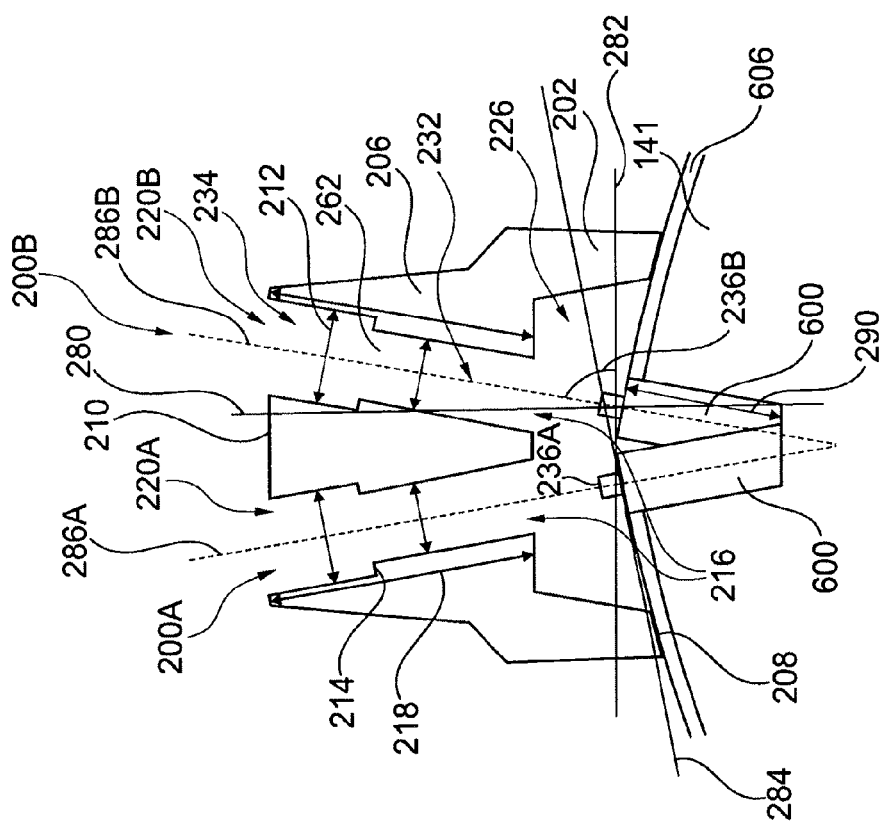
FIG. 5 shows an exemplifying embodiment of a sectional view of a guide tool according to the present invention.

FIG. 5 shows an exemplifying embodiment of a guide tool 1 according to the invention in a sectional view placed above cartilage damage. A guide tool 1 according to the invention is equipped with a guide body 206 comprising at least two guide channels, here shown as 200A and 200B. The guide channels 200A and 200B run through said guide body 206. The positioning body 202 has a cartilage contact surface 208 that has a shape and contour that is designed to correspond to and to fit the individual contour of the cartilage or the subchondral bone in the joint in a predetermined area surrounding the site of diseased cartilage in a patient. The guide tool 1 also has a top surface 210 facing approximately the opposite direction compared to the cartilage contacting surface 208. The guide body 206 extends from said positioning body 202 to said top surface 210 of the guide tool 1. In FIG. 2 the guide tool 1 is positioned on a representation of a femoral bone 141 over the cartilage damage site 806 with its positioning body 206 fitted above the area of the cartilage damage 92 placed on the surrounding cartilage 606. Each guide channel 200 in the guide tool 1 has an inner cross-sectional profile with a certain area. The cross-sectional area of the outer portion 234 is slightly larger than the cross-sectional area of the inner portion 232 or the cross-sectional area of the outer portion 234 may be 10% larger than the cross-sectional area of the inner portion 232.

Each guide channel 200 in the guide tool 1 has a height 218 of 0.3-20 cm or for example 3-10 cm.

The guide tool 1 is for example used to guide tools during the preparation of the cartilage damage site 806 in the patient in order to implant cartilage repair objects 600 for example implants or transplants or cartilage and bone plugs.

In one embodiment of the invention the guide channels 200 in the guide tool 1 has an inner cross-sectional profile, which is cylindrically formed with a certain diameter. The cross sectional diameter 212 of the guide channels 200 may be designed to correspond to the diameter of the tools to be used inside the guide channel 200. In other words, the tools used inside a guide channel 200, the insert tools, fit the guide channel 200, with a slight tolerance to allow a sliding movement of the tools in the guide channel 200.

The guide channels 200 of the guide tool 1 are in one embodiment constructed in a cylindrical shape, having an outer portion 234 with a diameter 212 and an inner portion 232 (close to the cartilage contact surface 208 of the guide tool 1) with a diameter 230. The diameters of the inner and outer portion may be the same diameter of (0.1-5 cm or 0.2-1 cm) or the diameter 212 of the outer portion 234 is between (0.1-5 cm or 0.2-1 cm) and slightly larger than the diameter 262 of the inner portion which is between (0.1-5 cm or 0.1-0.9 cm). In another embodiment, the diameter 262 of the inner portion 232 is 10% smaller than the diameter 212 of the outer portion 234.

The guide channels 200 inside the guide body 206 of the guide tool 1 according to the invention also comprise a stop function 214. The stop function 214 is used to regulate how deep a tool may be inserted inside the guide channel 200. In this way the stop function 214 regulates how deep an insert tool, for example a cartilage harvesting and insert tool 302 may be inserted in the guide body 206 or how deep the drill tool 304 may be inserted inside the guide body and thus how deep drill holes that may be created. The stop function 214 is located inside the guide channel 200 giving support to the insert tools above and beneath the location of the stop function 214.

Examples of insert tools used inside the guide channel 200 are shown in FIG. 3. FIG. 3 shows a cartilage harvesting and insert tool 302 comprising a plunger 308 used during placement of the transplant or implant, and a hollow body. The cartilage harvesting and insert tool 302 has corresponding stops 314, which together with the stop function 214 of the guide tool 1 regulate the use-depth of the tools used inside the guide channels (see FIG. 3). Additional depth adjustment of the cartilage harvesting and insert tool 302 is a depth control cylinder 306, which can be used to control the use of the stop function 314. FIG. 3 shows cartilage harvesting and insert tool 302 with the plunger 308 used inside the hollow body equipped with a depth control cylinder 306.

The guide tool 1 may in one embodiment be constructed in such a way that at least two guide channels 200 are placed above a non bearing part of the joint and at least one guide channel 200 is placed above the cartilage damage 92 in the joint. See FIG. 13 for an example, where the guide tool comprises guide channels constructed and placed for enable harvesting of cartilage plugs and also guide channels 200 constructed for guiding insertion of cartilage repair objects boo on the site of the cartilage damage 92.

The guide body 206 of the guide tool 1 has a mouth or muzzle 216, which is the guide channel's opening towards the cartilage surface. The mouth 216 is in a position facing the cartilage surface of the joint, corresponding to the site of the diseased cartilage in a joint. For example this diseased cartilage damage may have a size of 0.1 cm$^2$ and 5 cm$^2$, between 0.5 cm$^2$ and 3 cm$^2$, or preferably between about 0.5 cm$^2$ and 2 cm$^2$ or intended to repair cartilage damages of areas between 0.1-10 cm$^2$ or for example 0.1-4 cm.

The height 218 of the guide body 206 must be sufficiently long to give support to the insert tools used inside the guide body 206. The height 218 is preferably higher than the thickness of the surrounding tissue. In this way, the upper openings 220A and 220B of the guide channels 200A and 200B are easy to access for the surgeon. The height 218 of the guide body 206 is between 0.3-20 cm, or between 3-10 cm and always sufficiently high to ensure stabilization of the tools that are to be inserted into the guide channel 200.

The guide tool 1 according to the invention is preferably individually designed for a person's joint or designed to fit an average person's cartilage surface in a joint. The insert tools, for example the cartilage harvesting and insert tool 302 is also optionally individually designed for a specific person's cartilage individual injury.

The size and shape of cartilage contact surface 208 of the guide tool 1 is determined depending on the size and shape of the damaged cartilage. The size and shape of cartilage contact surface 208 of the guide tool 1 is also depending on the position of the cartilage area in a joint. The size and shape of the surface 208 is a consideration between the following aspects; minimize surgery lesion, maximize stability for guide tool 1, anatomic limitations on the site of the injury, not all cartilage surfaces in a joint can be used for placement of the guide tool 1. A large spread of the cartilage contact surface 208 is to prefer to get good stability of the guide tool 1, however, a large surface area of the contact surface 208 may also lead to a large surgical intervention and this is undesired. Thus the size of the cartilage contact surface 208 and of the positioning body 206 is determined by a balance between the desire to achieve good positioning stability and small surgical operations. Also, the cartilage contact surface 208 does not need to have a continuous, regular shape, but may have an irregular shape, as long as it gives adequate support and stable positioning of the guide tool 1.

The cartilage contact surface 208 may for example be 10-90% larger than the area of the muzzles of the guide channels. The guide tool (1) according to the invention comprises a guide channel (200) and a positioning body (206) which further comprises a cartilage contact surface (208). The positioning body (206) extends laterally outside the periphery of the guide channel (200). The extension laterally is depending on which spread and conformation of the positioning body that gives the most stability in the joint where the guide tool is to be placed (1). The design of the spread of the positioning body (206) of the guide tool (1) may be individually decided for in each individual joint.

When designing the guide tool 1, the cartilage contact surface 208 can be designed to cover three points (see FIG. 2, wherein one point 222 is marked by placement of a drill hole and the other two are marked by showing the pegs 224 that are to be inserted, see dotted lines in FIG. 2) distributed over the cartilage surface of the joint where the implant is to be inserted. The points are chosen to give maximum support and positional stability for the positioning body 202 and thus these points, either decided and identified by the surgeon or automatically identified by design software, serve the ground when designing the cartilage contact surface 208 of the guide tool 1. The cartilage contact surface 208 can also be formed such that it uses the curvature in the cartilage surface in a joint for stability. For example, in a knee joint, the condyles are separated from each other by a shallow depression, the posterior intercondyloid fossa, this curvature together with the medial epicondyle surface can be used to give the cartilage contact surface 208 a stabile attachment to the cartilage surface in a knee joint. Other surfaces surrounding the joint may also be used for attachment of the guide tool 1.

The surface is in one embodiment a continuous surface covering a selected area surrounding the cartilage damage 92. In another embodiment the cartilage contact surface 208 is distributed over a plurality of points, preferably three or more of separated contact points covering both the selected area surrounding the cartilage damage 92 and a selected area of the joint comprising a non bearing cartilage suitable for harvesting healthy cartilage plugs.

The cartilage contact surface 208 does not need to be a continuous, regular surface but preferably has at least three points exemplified in FIG. 2. Optionally the cartilage contacting surface 208 may be further stabilized by attachment with nails, rivets, pegs or similar attachment means to the bone surrounding the cartilage in a joint (see FIG. 2) but in other embodiments no such additional attachment of the guide tool is necessary. This additional attachment with rivets 224 or the like gives additional support and stability and also gives the possibility to keep the cartilage contact surface as small as possible. The position of the rivets may be predetermined and marked out by premade points or drill holes 222 on the positioning body.

The guide tool 1 may in one embodiment of the invention with exact precision guide removal of a volume of damaged cartilage and/or damaged subchondral bone from a joint. Preparation of the area comprising damaged cartilage may be prepared using a drill bit 304 inside the guide channels 200 of the guide tool 1, preparing a recess in a certain angle in the cartilage wherein a cartilage repair object 600 may be inserted.

The guide tool 1 may in one embodiment of the invention with exact precision and in a certain angle 236, guide insertion of a cartilage and/or subchondral bone plug or an implant from a selected area of the joint suitable for harvesting healthy cartilage.

The guide tool 1 may in one embodiment of the invention with exact precision, and in a certain angle 236, guide removal of a cartilage and/or subchondral bone plug from a selected area of the joint suitable for harvesting healthy cartilage.

The guide tool 1 may in one embodiment of the invention have at least one selected guide channel 200 dedicated to with exact precision and in a certain angle 236 guide removal of a cartilage and/or subchondral bone plug from a selected area of the joint suitable for harvesting healthy cartilage and also be configured to have other selected guide channels 200 dedicated to with exact precision, and in a certain angle 236 guide removal of a volume of damaged cartilage and/or damaged subchondral bone from a joint, for example by using insert tools inside the guide channels of the guide tool which are designed for removal or preparation of the cartilage damage site and with the same guide channels 200 also guide the insertion of said healthy cartilage plugs harvested from a non bearing part of the joint, see FIG. 13.

In different embodiments, each guide channel is oriented such that the longitudinal axis of the guide channel is inclined at a selected angle between 0-40 degrees in relation to the normal of a tangential plane drawn at a point at the articulate surface of the cartilage or of the bone where the axis of the channels intersect the articulate surface. Neighboring guide channels may have different inclination angles. For example, as in the embodiment illustrated in FIG. 5, a first, channel 200A has a longitudinal axis 286A having an inclination angle of 0 degrees, i.e. the axis 286A (with tangential plane 284) coincides with the normal, whereas the longitudinal axis 286B (with tangential plane 282) of a second channel 200B has an inclination angle of 20 degrees (compared to normal 280). When using the guide tool according to this example to drill recesses in a joint bone the result is two recesses having different angles in relation to the articulate surface and to each other.

For example the guide channels are designed to be oriented such that the longitudinal axis of the guide channel is inclined at a selected angle between 0-40 degrees in relation to the normal of a tangential plane drawn at a point at the articulate surface of the cartilage or of the bone where the axis of the channels intersect the articulate surface and in this way providing a desired and exact repair of the cartilage damage site.

The angle 236 may be selected so that the cartilage repair object 600 fit into the damaged area to be repaired or so that the healthy cartilage plugs are harvested at selected inclination angles 236. The angle 236 and location of the guide channels 200 inside the guide body 206 of the guide tool may also be selected so that the cartilage repair objects 600 fits with a certain angle in respect to the damage and also in respect to other cartilage repair objects 600 in a mosaic pattern into the damaged area to be repaired, see for example FIG. 5.

The guide channels 200 of the guide tool 1 are also individually designed and are used to guide removal of damaged cartilage and the guide channels 200 have in one embodiment a stop function 214 which may be used to guide removal of damaged cartilage in a certain depth from the damaged cartilage site. The guide channels 200 of the guide tool 1 are individually designed and are used to guide insertion of cartilage repair objects 600 in a certain angle 236, to a certain depth 290 into the damaged cartilage site.

The guide tool 1 is manufactured using a suitable material or materials that is/are approved for use in medical procedures, e.g. a ceramic, plastic, metal, metal alloy or aluminia material, or a combination. The guide tool 1, especially the cartilage contact surface 208, is also preferably made of a material that is smooth, even and/or has low friction, in order to lessen the risk of wear and damage to the cartilage on which it is to be placed. Such materials include e.g. metals, ceramics and polymers such as acrylonitrile butadiene styrene (ABS) or polyamid for example nylon or glass filled nylon or epoxy materials clear or not clear. The used materials may further be polished.

FIG. 5 shows an exemplified embodiment of the guide tool 1 wherein the guide body 206 comprises a hollow space 226 at the foot inside the guide body 206. The hollow space 226 is designed to enable output of waste such as cartilage tissue and bone chips from boring or reaming in the preparation of the recess for the implant in the joint and/or also designed so that the surgeon easier can see the cartilage damage site.

The Plug Harvesting and/or Insertion Tool

The plug harvesting and insertion tool 302 is an insert tool which may be used to cut out the cartilage in the joint around the area of damaged cartilage to prepare for the insertion of the implant, see FIG. 3.

In another embodiment of the invention the plug harvesting and insert tool 302 is an insert tool which may be used to cut out the cartilage in a non bearing part of the joint or to cut out an implant is and then used to transfer the collected healthy cartilage to a cartilage damage site 806 (which has been prepared for retrieving the healthy cartilage and bone plugs). The plug harvesting and insertion tool 302 is then used to place the retrieved healthy cartilage and bone plug or the implant in the cartilage damage site 806 using a plunger 308 inside the hollow body 310 of the plug harvesting and insertion tool 302, see FIG. 8E-F.

In another embodiment the plug harvesting and insertion tool 302 may for example comprise of a sharp edge which is able to punch or cut cartilage and or bone, the sharp edge may be cylinder shaped and allow the harvested cartilage and bone plug to be stored inside the harvesting tool body 312. The plug harvesting and insertion tool 302 is used inside the guide channel 200 of the guide tool 1 and fits in the guide channel 200, with a slight tolerance to allow a sliding movement of the plug harvesting and insert tool 302 inside the guide channel 200. The plug harvesting and insertion tool 302 preferably cuts the cartilage so that the cut edges of the harvested cartilage and bone plugs are sharp and smooth.

In one exemplifying embodiment of the invention the plug harvesting and insertion tool 302 is used as a punch. The plug harvesting and insertion tool 302 is a solid body with a hollow shape or recess 330 in one end. The recess 330 has sharp edges 332. The plug harvesting and insertion tool 302 is used to punch out, healthy cartilage from the non bearing surface of a joint. The plug harvesting and insertion tool 302 is to be placed inside the guide channel 200 of the guide tool 12, with the recess 330 pointing down onto the cartilage. A hammer is then used to hammer the recess 330 of the plug harvesting and insertion tool 302 through the cartilage. In this way the damaged cartilage is removed by punching. The depth of the removed cartilage may be adjusted to the individual person's needs and is controlled by the stop function 314 inside the guide channels 200 of the guide tool 1 in combination with the stop function 314 of the cartilage harvesting and insert tool 302.

It is of great importance that the plug harvesting and insertion tool 302 has sharp cutting edges. The material of the sharp edge of the plug harvesting and insertion tool 302 is chosen from materials which may stable to withstand the pressure when it is hammered into the cartilage and bone. Examples of such materials are metals such as stainless steel or ceramic material or a plastic material or a hard coated material.

The cross-sectional profile of the plug harvesting and insertion tool 302 varies in different realizations of the invention between 0.1 cm$^2$ and 5 cm$^2$, between 0.5 cm$^2$ and 3 cm$^2$, or preferably between about 0.5 cm$^2$ and 2 cm$^2$.

The length 334 of the plug harvesting and insertion tool 302 is longer than the height 218 of the guide channel 200. The height 240 of the inner part 232 of the guide channel 200 is shorter than the length 336 of the lower part or the narrower part 312 of the plug harvesting and insertion tool 302. The difference in length between the inner part 232 of the guide channel 200 and the length 336 of the lower part or the narrower part 312 of the plug harvesting and insertion tool 302 corresponds to the length of the cartilage plug to be retrieved.

The Drill Bit 304

In one exemplifying embodiment of the invention the insert tool is a drill bit 304, see FIG. 3. The drill bit 304 is used to remove the damaged cartilage and bone in the joint around the area of damaged cartilage to prepare for the insertion of the implant.

The drill bit 304 comprises an upper drill body 324 with a tolerance enabling the upper drill body 324 to slide within the guide channel 200. The upper drill body 324 has a cross-sectional profile that is designed to correspond to the inner cross-sectional profile of the outer part 234 of the guide channel 200 with a tolerance enabling the upper drill body 324 to slide within the guide channel 200. The drill bit 304 also comprises a lower drill body 344, which is the drill blade. Also, the cross-sectional profile of the lower drill body 344 is designed to correspond to the cross-section of the implant placed inside the made drill hole.

In one embodiment of the present invention the surgical kit comprises a drill bit 304 that is used for drilling a hole in the bone at the site of cartilage damage, for fastening of cartilage repair objects 600.

The drill bit 304 has a depth gauge or a stop function 316. The stop function 316 on the drill bit 304 is supported by the stop function 214 inside the guide channel 200 and by using this support the depth of the drill hole can be controlled and used to give drill-hole in the bone with an exact position and depth and direction.

Control Lock

Figure 6:
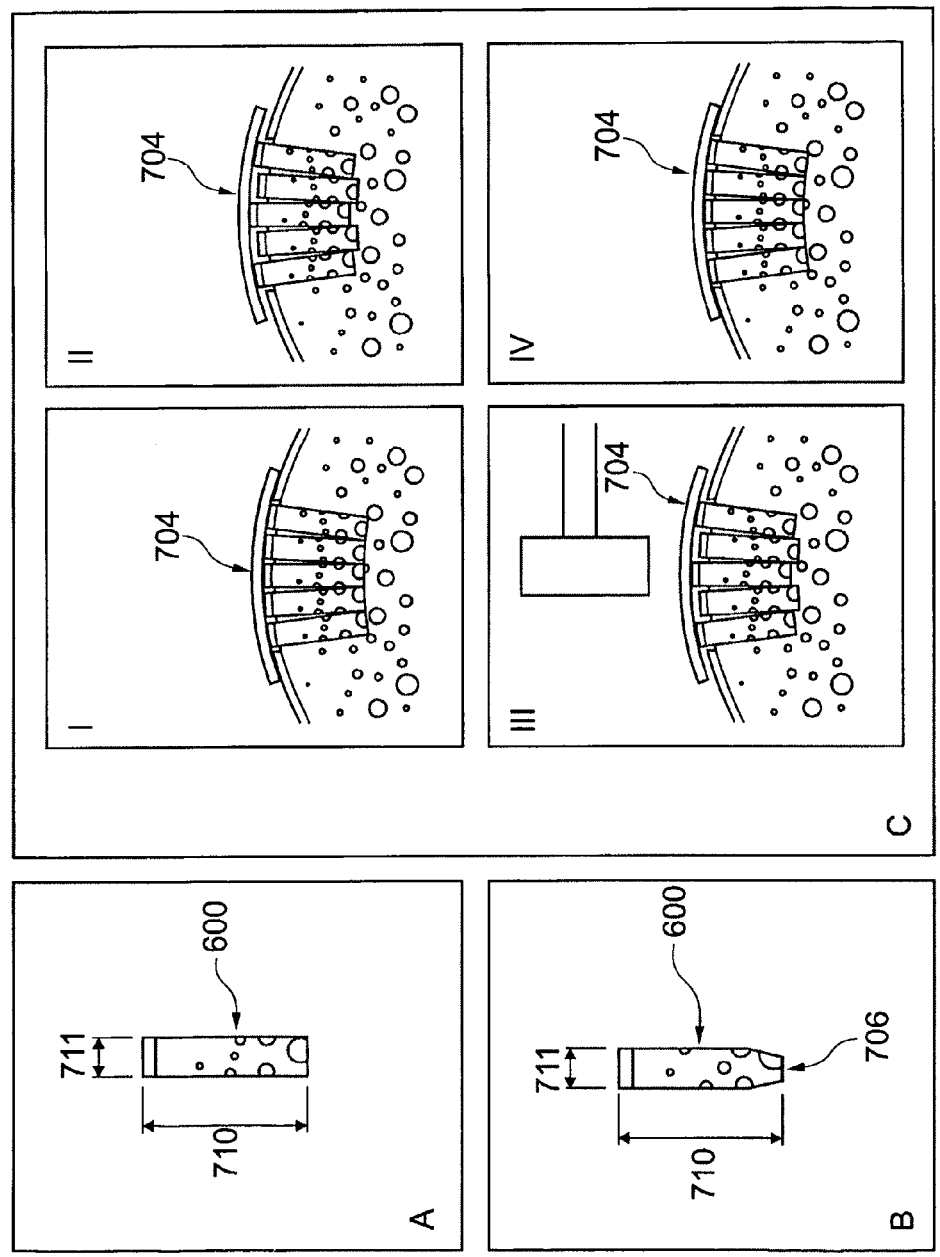
FIG. 6a-c show exemplifying embodiments of cartilage repair object and a control lock tools used during mosaic implantation according to the invention.

The control lock 704 is used to adjust the placed cartilage and bone plugs after placement, see FIG. 6c. The shape of the control lock mimics the shape of a healthy cartilage surface. The control lock is used by placing the control lock on top of all the cartilage repair objects 600 and then by the force of a hammer placing all plugs in the same level as the surrounding cartilage.

The control lock is individually designed to correspond or mimic to the actual healthy cartilage surface of the cartilage in the area of the cartilage damage.

The control lock may be made using a suitable material or materials that is/are approved for use in medical procedures, e.g. a ceramic, plastic, metal, metal alloy or aluminia material, or a combination.

Healthy Cartilage Plugs or Implants

FIG. 6a-b show a healthy cartilage and bone plug removed from a non bearing part of a joint using a guide according to the invention together with a harvesting an insert tool.

The healthy cartilage plugs harvested guided by the guide tool 1 according to the invention may be further reshaped after harvesting by using a sharpener tool. The sharpener tool may be constructed as a pencil sharpener, with a sharp blade, but which may be used to adjust the shape and/or the length of the bone part of the harvested cartilage plugs so that several plugs may be suited together in an area of cartilage damage. FIG. 6a shows a harvested healthy cartilage plug 600, FIG. 6b shows a harvested healthy cartilage plug sharpened using a sharpener tool according to the invention, FIG. 6c shows a cartilage damage site repaired using mosaic repair technique, which includes using several healthy cartilage plugs which may be sharpened using the sharpener tool before insertion, which makes the cartilage plugs to fit better in the damaged area of the cartilage, FIG. 6c also shows the use of the control lock 704.

According to an embodiment of the present invention the amounts of plugs and also the size and shape of the healthy cartilage and bone plugs are selected depending on the shape and size of the injury.

The healthy cartilage plugs 600 harvested according to the invention or implants used according to the invention has a cross sectional area between 0.5 cm$^2$ and 5 cm$^2$, between 0.5 cm$^2$ and 3 cm$^2$, or preferably between about 0.5 cm$^2$ and 2 cm$^2$ and a length 710 between 1-4 cm, or between 1.5-3 cm.

The healthy cartilage plugs 600 harvested according to the invention or implants used according to the invention has a cross sectional diameter 711 between for example 0.1-1 cm and length 710.

The healthy cartilage and bone plug is specially designed, depending on the knees appearance and also the shape of the damage and in order to resemble the body's own parts, having a surface which preferably corresponds to an image of a simulated healthy cartilage surface. The implant will be tailor-harvested, for example by using the guide tool according to the invention from a non bearing cartilage area to fit each patient's damaged part of the joint.

The primary factor for determining the size of the healthy cartilage bone plugs is however the nature of the lesion to be repaired.

Use of the Guide Tool and the Insert Tools According to the Invention

This invention provides a guide tool 1, where the successful cartilage repair object insertion is less depending on the skills of the surgeon compared to previously known methods. This invention provides preferably an individually designed guide tool 1. Due to the design and the function of the guide tool 1, improved implantation precision and a precise desired placement of the implant in the joint is achieved every time. The precision of the surgery is "built in" into the design of the guide tool.

The guide tool of the invention, which may be individually adapted to fit in person's knee or other joints and leads to shorter learning curves for the surgeon since the guide tool adapted to fit the injury as well as the other surgical tools, giving precise guidance, facilitates for quick, simple and reproducible surgery.

In one exemplifying embodiment the healthy cartilage and bone plugs are intended for replacing damaged cartilage in a knee. The site where the healthy cartilage and bone plugs is to be implanted according to the invention is an articular cartilage surface including, for example, the lateral femoral chondral (ITC) surfaces, medial femoral chondral (MFC) surfaces, trochlea surfaces, patella surfaces, tibia surfaces (e.g. surfaces of the tuberosities of the tibia), and combinations and portions thereof. For example healthy cartilage and bone plugs may be placed on any one of these surfaces.

The site where the healthy cartilage and bone plugs are harvested according to the invention is non-bearing cartilage surfaces, and combinations and portions thereof.

The healthy cartilage and bone plugs are inserted through a small open surgery operation using a guide tool, which preferably may be individually designed or tailor/custom made for the person who suffers from the injury. Further the guide tool is tailor/custom made to fit the cartilage harvesting and insert tool 302 and also to fit the cartilage area to be repaired.

This leads to decreased suffering of the patient and is economically favorable since it leads to shorter convalescence time and less time for the patient at the hospital. By using this optionally individually designed guide tool together with a cartilage harvesting and insert tool 302 the implant insertion will be optimal and thus misalignment, which is one of the problems associated with the common methods used today can be avoided.

The object of the invention is to solve the problem of repairing damaged cartilage by providing cartilage repair objects 600 that will have better placement and that will be better aligned and supported thus giving a fitted placement in the cartilage.

Figure 7:
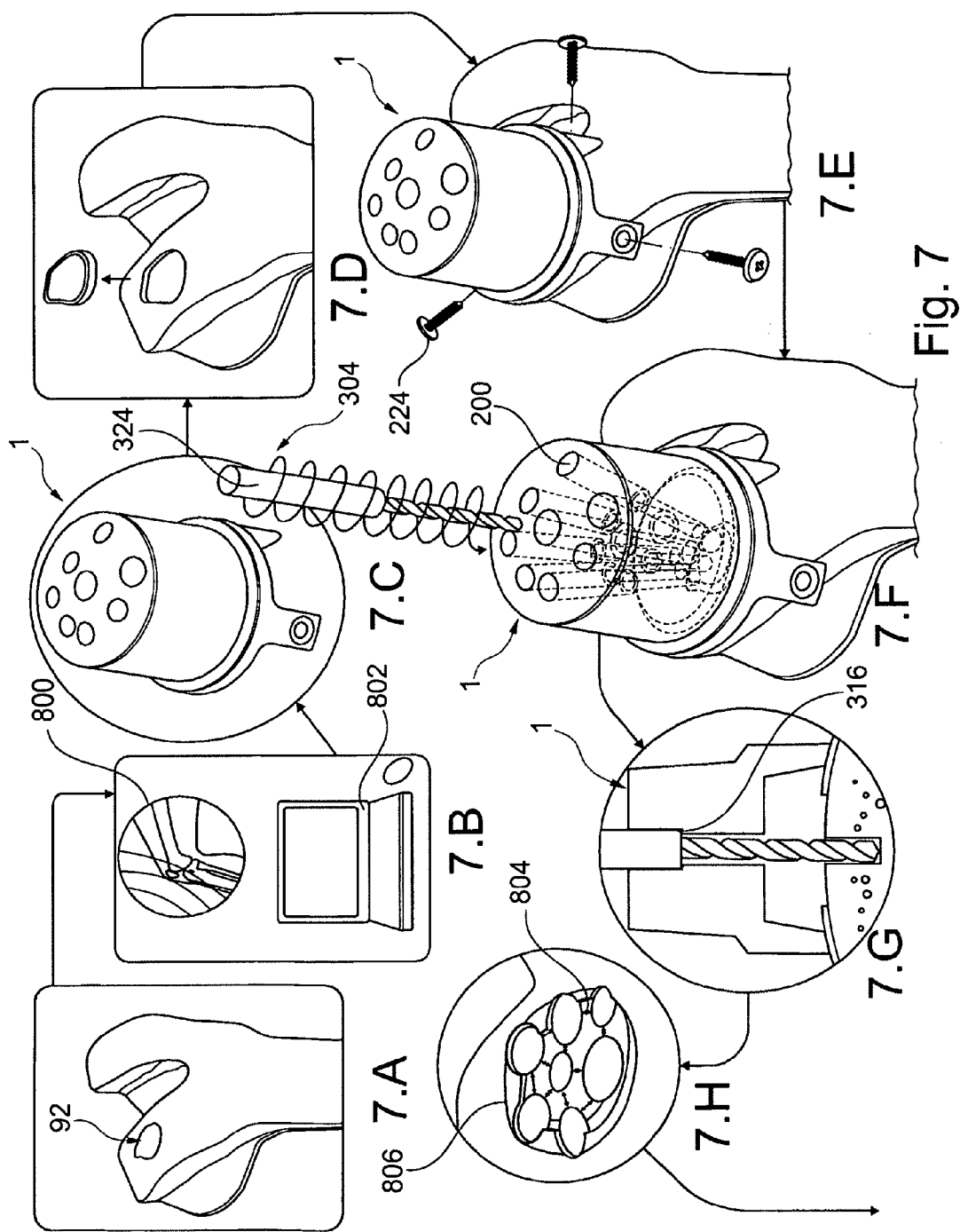
FIG. 7A-H show an exemplifying embodiment of a surgical method using the guide tool according to the invention.

Detailed Description of a Method for Implanting the Implant Using the Guide Tool See FIG. 7.

FIG. 7A-B. Localize the area of the injury, the cartilage damage 92 and determine the desired size and shape of the healthy cartilage plugs. The position and size of the cartilage damage can be identified by a combination of MRI or CT images or by dGEMRIC technique 800. The images may then be handled in special surgical planning tool software 802. All of the parts in the surgical kit may be individual adjusted depending on size of cartilage damage, location of the cartilage damage and also depending on a simulation of the individual surface-appearance without damage. The surgical planning tool software 802 may also be used for planning the placement, angle surface curvature and depth of the healthy cartilage plugs in the place of the injury.

Alternatively implants from a set of predetermined implants may be selected for repair of the cartilage damage 92 instead of using harvested cartilage and bone plugs. The shapes of the surgical tools are also adjusted to the selected implants or plugs. See FIG. 7A-7C. The guide tool 1 of the invention is manufactured depending on;

the size of the implants or cartilage and bone plugs needed,
the localization of the injury,
the appearance of the cartilage surface and/or bone intended to be replaced.
the placement of the implants in relation to the injury site and also in relation to each other and in a certain angle and depth.
the harvesting site (non bearing cartilage in a joint wherefrom the healthy cartilage plugs are harvested)

The insert tools are manufactured depending on the selected choices for the guide tool and also depending on the selected sizes for the implants or healthy cartilage plugs.

The designs may be based on the MR images/CT-scanning images from the joint of the person having the cartilage damage, using the surgical planning software. The surgical planning software is connected to manufacturing devices, for example a laser printer, a lathe and/or a reamer, and the parts of the kit are manufactured using e.g. additive manufacturing, laser sintering techniques, turnery or reaming.

Additionally a control lock 704 may be designed according to a simulated healthy cartilage surface of the cartilage damage site 92 of a patient.

7D. A surgical opening is made in the leg tissue depending on the localization of the injury and the size of the implant and also depending on the size and conformation of the guide tool. Alternatively the damaged cartilage layer is removed.

7E. The guide-tool 1 is placed on the surface of the knee cartilage. The guide-tool 1 fits due to the fact that it is custom made to be placed in that particular position. This allows the surgical procedure (cartilage and bone removal and insertion of the healthy cartilage plugs or implant or harvesting of the healthy cartilage plugs) to be performed with good accuracy and precision. If necessary the guide tool can be further stabilized with rivets 224 on a part of the guide tool that is in contact with parts of the joint that have no cartilage tissue.

7F. After the guide tool 12 has been placed on the cartilage through an opening in the surrounding tissue, the drill bit 304, may optionally be used to drill out a recess of the cartilage. The upper part 324 of the drill bit 304 fits exactly in the upper part 234 of the guide channel 200 and thus can make a hole in the cartilage and/or bone of the desired size, depth, and angle with precision to fit the implant or healthy cartilage plugs size and at the desired position and angle.

7G-H The drill bit 304 is then inserted in the guide channel 200. The drill bit 304 may comprise a stop function 316 which may be used inside the guide channel 200 to give an exact, desired placement of the bore in the bone where the cartilage repair object boo is to be attached. The recess may be made with a smaller diameter than the diameter of the of the cartilage repair object so that when the cartilage repair object is hammered in place it will be firmly attached in the bone. Optionally the removal of damaged cartilage and preparation of recesses for placement of the implants can be done using the cartilage harvesting and insert tool 302 or a reamer bit.

After the guide tool is used to guide the drilling of recesses in the bone the site to be repaired has recesses placed preferably with 1-3 mm as shortest distance 804 relative to each other. This recess placement is planned for already in step 7B.

Figure 8:
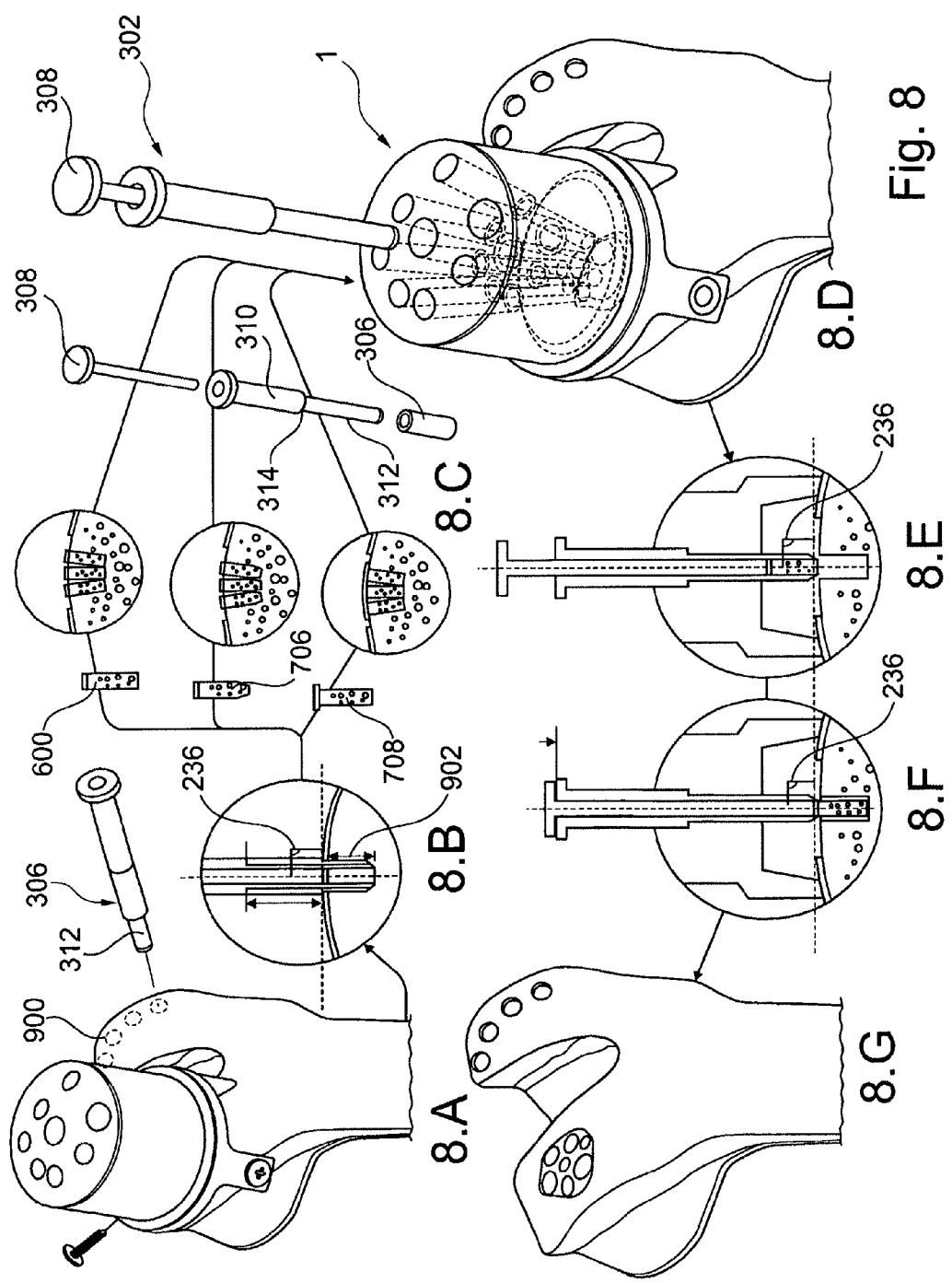
FIG. 8A-G show an exemplifying embodiment continuation of a surgical method using the guide tool according to the invention.

See FIG. 8

8A. Shows an exemplified embodiment of a desired area 900 for harvesting of healthy cartilage and bone plugs which may be used for repairing the cartilage damage. The harvesting may be performed using a cartilage harvesting and insert tool 302 inside the guide tool 1 or the harvesting may be performed as demonstrated in step 8A using the cartilage harvesting and insert tool 302 without the guide tool.

The depth 290 that the cartilage harvesting and insert tool 302 is entered into the cartilage is dependent on depth control cylinder 306 which is attached on the narrower part 312 of the cartilage harvesting and insert tool 302 and supported by the stop function 314 of the cartilage harvesting and insert tool 302. The difference in length 902 between the length 350 of the depth control cylinder 306 and the length 336 of the narrow part 312 of the cartilage harvesting and insert tool 302 determines the length of the harvested healthy cartilage plugs.

8C. Demonstrates that the harvested cartilage plugs may be shaped using a sharpener tool 700 so that the bone part of the harvested cartilage plug can be slightly sharpened as can be seen in the sharpened cartilage and bone plug 706. The cartilage repair objects may also be adjusted in length using the sharpener tool. The harvested cartilage plugs may in this way be easier to place and with a better alignment to each other. In another embodiment of the invention the harvested cartilage plugs are turned so that the cartilage has a larger cross sectional area than the underlying bone (see 708) of the harvested cartilage plug.

8D-F. After the recesses for the implants are made and optionally as described in step 8A-C, the healthy cartilage implant plugs are harvested and also optionally shaped, the guide tool 1 is used for example together with the cartilage harvesting and insert tool 302 for placement of the harvested implants into the exact matching drilled recesses. The cartilage harvesting and insert tool 302 is used together with a plunger 308 during the placement of the harvested implant plugs. The plunger 308 is placed inside the cartilage harvesting and inserts tool body 310 and 312 and the harvested cartilage plug, placed inside the cartilage harvesting and insert tool 302 is pushed out and placed in the recess made in step 7G FIG. 7. A hammer may be used on top of the plunger 308 for the placement of the healthy cartilage plugs in the recess, see step 8E-F.

8G. Shows the cartilage damage site after the cartilage repair according to the method of the invention. Optionally a control lock 704 (seen in FIG. 6*d*) may be used on top of the placed implants to further adjust the surface of the implant plugs to the desired cartilage surface in the patient before the injury.

Detailed Description of a Design Method for Designing the Guide Tool

FIG. 4 schematically illustrates the design process according to an embodiment of the inventive concept for designing a surgical kit. The design system comprises the basic blocks of:

I. Determining physical parameters by obtaining an image 91 for a cartilage damage 92 of a joint in a body part or limb 98 of a patient. Determine physical parameters for cartilage damage 92 in joint and generating design parameters for cartilage repair objects 600.

II. Generating design parameters 95 of a guide tool 1 to be used for placement of cartilage repair objects 600 and alternatively also for retrieving healthy cartilage and bone plugs from a non bearing part of a joint.

The physical parameters as well as the design parameters are represented as digital data that is processed or generated by specifically designed computer program code portions executed in a data processing system. The system may be fully automated or may comprise portions of computer supported manual steps of for example selections, scymutation or capping. The design parameters resulting from the process are stored in a format suitable for use as input in drawings normally STL or STEP etc. format in a manufacturing process.

I. Determine Physical Parameters for Cartilage Damage 92 in a Joint and Generating Design Parameters for Cartilage Repair Objects 600.

An image or a plurality of images 91 representing a three dimensional image of a bone member of the joint in a patient's limb 98 is obtained by a selected one of a per se known imaging technology for non-invasive imaging of joints, such as magnetic resonance imaging (MRI), computerized tomography (CT) imaging or a combination of both, or other suitable techniques such as delayed Gadolinium-enhanced MRI of cartilage (dGEMRIC) techniques. The image of the joint should comprise a representation of cartilage in the joint as well as the underlying subchondral bone in the area of the cartilage damage. Image data making up a three dimensional image representation of the joint is stored in a digital format in a manner that enables to keep track of the dimensions of the real joint that the image depicts.

The image data 94 is analyzed in a data processing system 93 to identify and determine physical parameters for the cartilage damage 92. The physical parameters to determine comprise the presence, the location and the size and shape of the cartilage damage 92, as well as curvature of the surface contour of the cartilage or the subchondral bone in an area of the cartilage damage 92; i.e. determining the cartilage damage site 806.

The inventive concept the design system operates to determine physical parameters on images 91 of the patient's individual joint and the current cartilage damage, and thereby produces an individually designed guide tool 1.

The following steps are in one embodiment comprised in determining physical parameters for cartilage damage in a joint and generating design parameters for cartilage repair objects boo and their relative placement in a predetermined pattern, comprising:

a. obtaining image data 94 representing a three dimensional image of a bone member of the joint.

Figure 9:
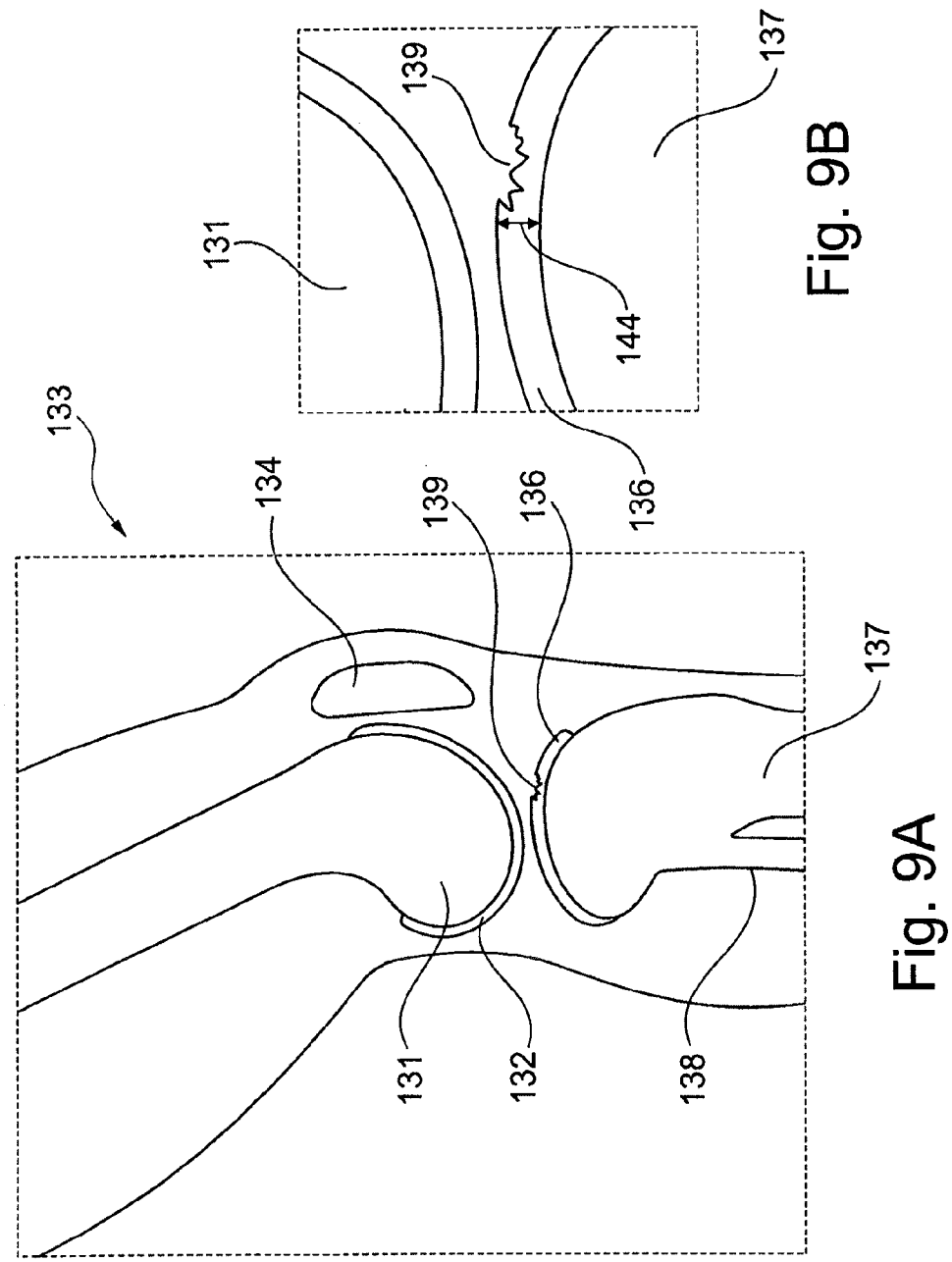
FIG. 9A-B show an exemplifying embodiment of cartilage damage in the tibia bone. The figure represents a sample image, in a side view, from a set of several images which together represent a three dimensional image of a joint.
Figure 12:
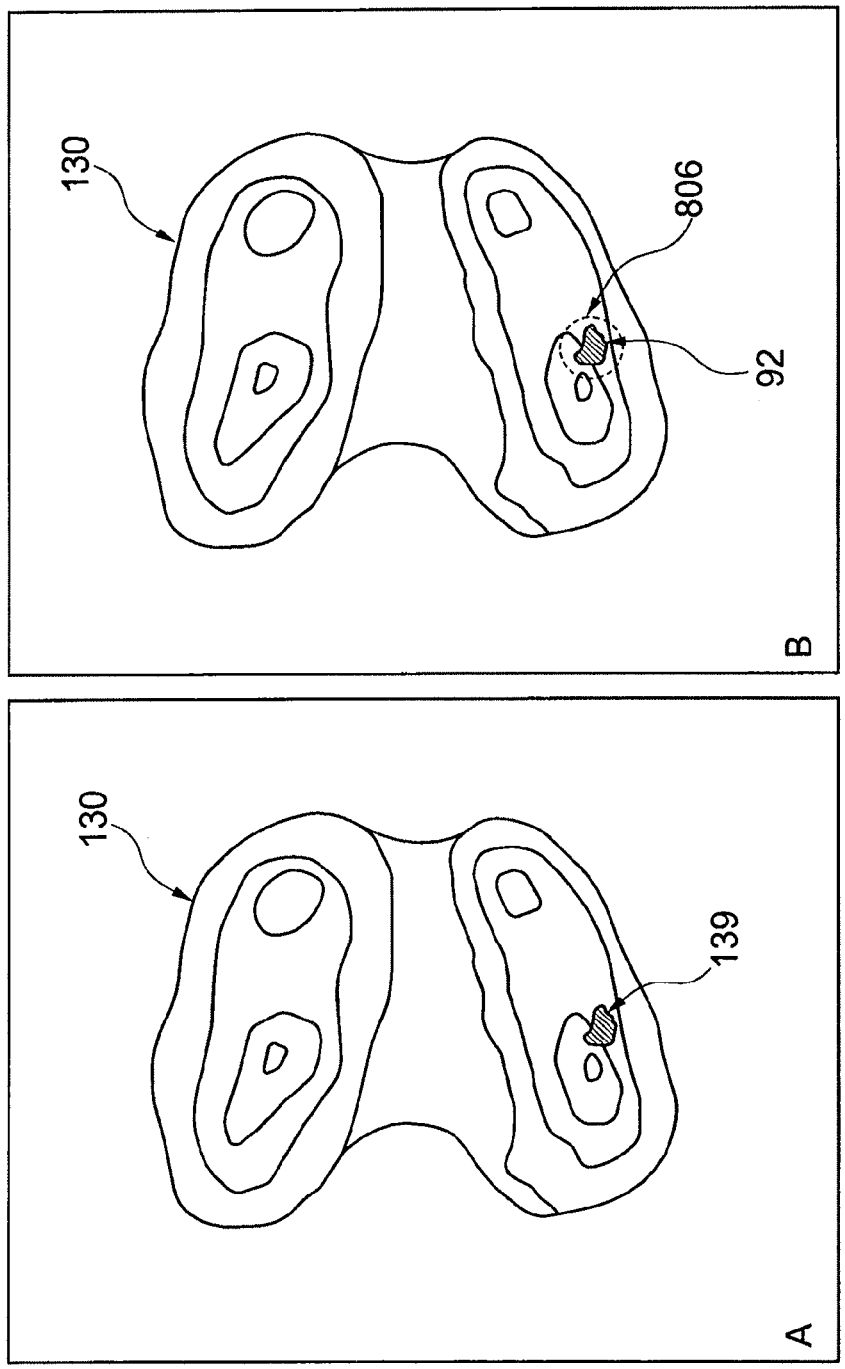
FIG. 12A-B show examples of a front view of the articular cartilage parts of the femur bone.

By way of example, FIG. 9 illustrates schematically a sample of a set of several images which together represents a three dimensional image of a joint. FIG. 9A shows a cross-section of a knee joint 133 with a femur bone 131, a patella bone 134, a tibia bone 137 and a fibula bone 138. Articular cartilage 132 and 136 is found on the femur and the tibia bone, respectively. FIG. 12A-B shows a front view of the articular cartilage parts 130 of the femur bone comprising cartilage damage 92 and a cartilage damage site 806.

b. identifying in the obtained image data 94 an individual cartilage damage 92 in an articulate surface of the bone member;

In an automated process a computer program would be adapted to scan the image data for predetermined characteristics of a spot of cartilage damage 92 in the image data. In a process with a manual part in this step an operator would visually scan a displayed image of the joint and identify a spot that has the visual characteristics of cartilage damage 92. FIG. 9A shows an example of cartilage damage 92 in the tibia bone and FIG. 9B shows an example of cartilage damage 92 and a determined cartilage damage site 806 in the femur bone in a front view.

c. determining based on the obtained image data 94 the location of the individual cartilage damage 92; a set of data that represents a position of the cartilage damage in the joint is selected automatically or manually. The position data is for example stored as a set of defined coordinates in the image data.

d. determining based on the obtained image data 94 the size and shape of the individual cartilage damage 92;

e. determining a cartilage damage site 806 based on the determined size and shape of the cartilage damage 92; Selected measurements for size and shape of the cartilage damage 92 are calculated in the image data 94, for example by determining a boundary line for the healthy cartilage surrounding the cartilage damage 92. FIG. 12B illustrates as an example of how a predetermined or selected circular cross-section shape 806 having a two-dimensional extension is automatically or partly manually matched over the cartilage damage. FIG. 9B illustrates an example of that the thickness 144 of healthy cartilage is determined around the perimeter of the cartilage damage site 806 extending over the cartilage damage 92. The size and shape data is for example stored as a set of perimeter and thickness data with a predetermined resolution.

f. determining based on the obtained image data 94 the surface contour curvature of the individual cartilage damage site 806 and/or the subchondral bone in the joint in the predetermined area comprising the individual cartilage damage site 806. The curvature of the surface contour is determined for example by per se known surface matching methods in image processing or manually by drawing a drawing of a curvature which is intended to fit the individual cartilage damage site 806. The determined curvature information can be represented as an equation or as a set of image data. The determined curvature preferably comprises two subsets of curvature information. Firstly, one subset comprises the curvature of the contour portion that comprises the cartilage damage site 806 defining the selected boundary line for the area covering the cartilage damage. Secondly, the second subset comprises the curvature of a contour portion that surrounds the site of cartilage damage, preferably comprising mutually opposing sloping parts.

g. Determining a representation of a healthy surface contour curvature comprising the individual cartilage damage site h. Selecting repair objects to fit the individual cartilage damage site 806 wherein the cartilage repair objects 600 have;
   cross sectional areas adapted to fit the surface area of the cartilage damage site
   lengths 290 adapted to fit the selected joint and/or type of cartilage damage
   surfaces intended to be aligned with the articular cartilage surface in the joint, based on the healthy surface contour curvature.

i. Determining, based on the obtained image data, positions and angles of the selected cartilage repair objects 600, wherein the positions and angles are adapted so that the selected repair objects fit the individual cartilage damage site 806.

II. Generating Design Parameters 95 of a Guide Tool 1 to be Used for Placement of Cartilage Repair Objects 600 and Alternatively Also for Retrieving Healthy Cartilage and Bone Plugs From a Non Bearing Part of a Joint.

Generation of design parameters of a guide tool 1 is based on the physical parameters for the cartilage damage 92 and surrounding tissues and design parameters for a cartilage repair object 600 which are generated by processing the physical parameters in a design stage 95 according to a predetermined scheme for the shape of an implant in the specific surgical application see step I.

The following steps are in one embodiment comprised in generating design parameters for a guide tool 1:

a. Generating the contact points for a cartilage contact surface 208 of a positioning body 206 dependent on said determined surface contour curvature of the cartilage and/or the subchondral bone in the joint in a predetermined area comprising and surrounding the site of cartilage damage, such that said cartilage contact surface 208 of the positioning body 206 fits to said individual surface contour of the cartilage or the sub-chondral bone in the joint and/or to a simulated healthy cartilage surface of an individual joint.

b. Generating the design for a upper part 234 and a lower part 232 of a guide channel 200 in a guide body 206 extending from the positioning body 202, said guide channel 200 passing through said positioning body 202 and said guide body 206 wherein the angles and positions is generated dependent on and substantially corresponding to the determined angles and positions of the selected cartilage repair objects, and wherein;
   the design for the lower part 232 of all the guide channel 200 is generated dependent on and substantially corresponding to the determined cross sectional areas, of the selected cartilage repair objects 600. In different embodiments, each guide channel is oriented such that the longitudinal axis of the guide channel is inclined at a selected angle between 0-40 degrees in relation to the normal of a tangential plane drawn at a point at the articulate surface of the cartilage or of the bone where the axis of the channels intersect the articulate surface. Neighboring guide channels may have different inclination angles. For example, as in the embodiment illustrated in FIG. 5, a first channel 200A has a longitudinal axis 286A having an inclination angle of 0 degrees, i.e. the axis 286A coincides with the normal, whereas the longitudinal axis 286B of a second channel 200B has an inclination angle of 20 degrees. When using the guide tool according to this example to drill recesses in a joint bone the result is two recesses having different angles in relation to the articulate surface and to each other.

Figure 10:
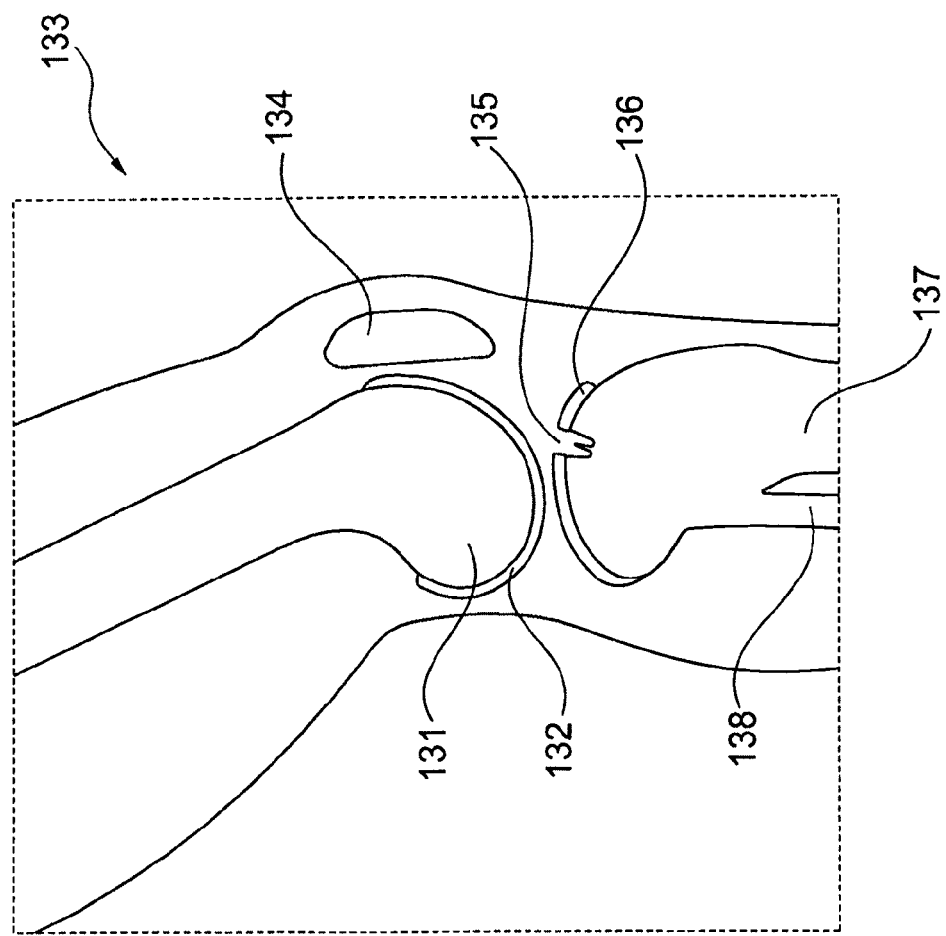
FIG. 10 shows schematically in an exemplifying embodiment of the invention how image based tools of the invention may be used to visualize in an image a model of a recess in the cartilage and the subchondral bone for an implant.
Figure 11:
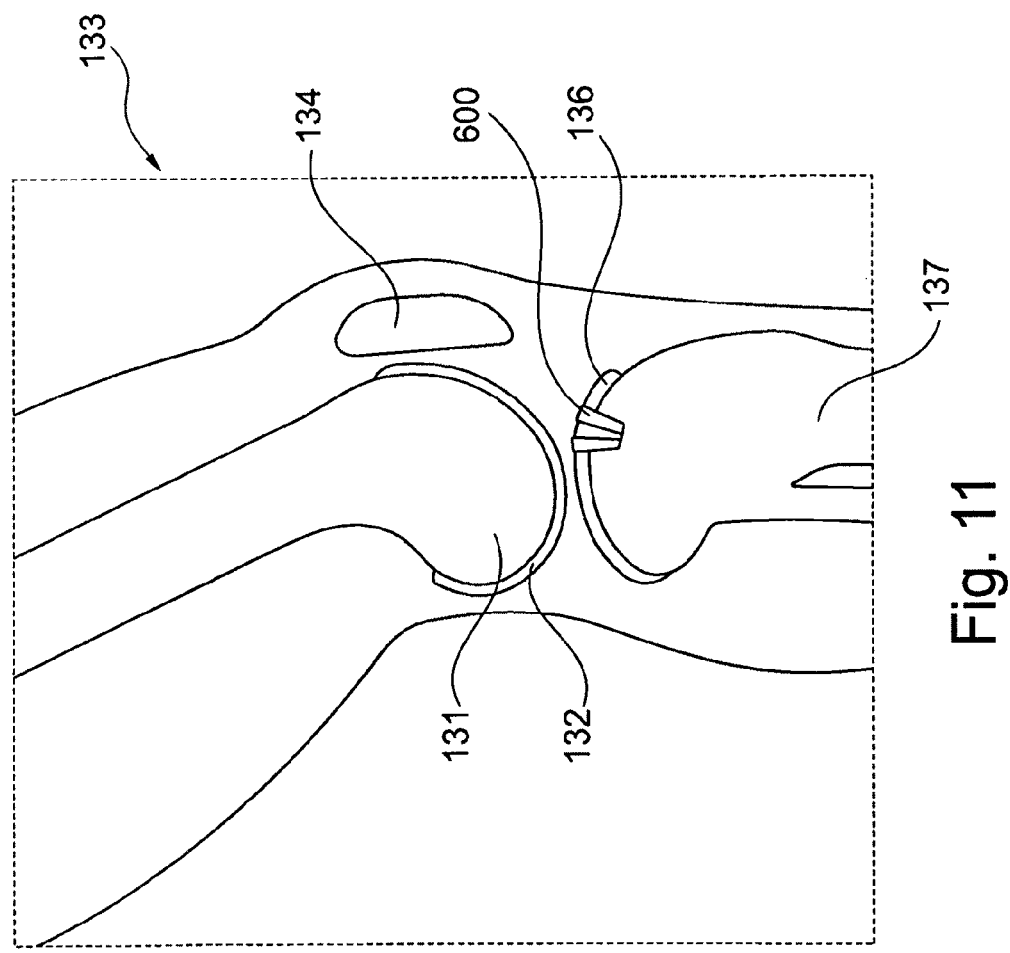
FIG. 11 shows schematically in an exemplifying embodiment of the invention how image based tools of the invention may be used to visualize in an image a model of an inserted cartilage repair object according to the generated design parameters.

FIG. 10 shows schematically how image based tools of the invention may be used to visualize in an image a model of a recess 135 in the cartilage and the subchondral bone for two healthy cartilage repair objects 600 and FIG. 11 shows a cartilage repair site with inserted cartilage repair objects 600 according to the generated design parameters. The image based tool may also be configured for using predetermined shapes of cartilage repair objects that are adapted to the determined physical parameters to automatically or manually fit to the cartilage damage site 806 and thereby generate the design parameters.

Further Embodiments

Embodiments of the invention further comprise optional combinations of the following:

b. Generating design parameters for the drill bit comprises generating dimensions and position for a depth control cylinder on the drill bit 304 for adjustment of the depth of drilling. Generating dimensions of the upper part 324 of a drill bit with a cross-sectional profile that substantially corresponds to the cross-sectional profile of the cartilage repair object 600 to be placed in the recess or to the cross-sectional profile of the guide channel 200 wherein the drill bit 304 is to be used. In one embodiment the drill bit 302 is designed to fit a selected guide channel 200 and also designed to give a desired depth of the drill hole by selecting the design of the control stop function 316 of the drill bit 302 c. Generating design parameters for a cartilage harvesting and insert tool 302 which comprises generating design parameters cartilage harvesting and insert tool 302 having an end with a cutting surface 332, said end having a recess 330 with a cross-sectional profile that substantially corresponds to the cross-section of the cartilage repair object to be placed in the recess. Generating dimensions and position for a control stop function 316 on the drill bit 304 for adjustment of the depth of drilling depending on the size and dimensions of the upper part 234 of the guide channel 200 wherein the cartilage harvesting and insert tool 302 is to be used, wherein the cross-sectional diameter (262) of the inner portion (232) of the guide channel 200 is smaller than the cross-sectional diameter 396 for the upper part 324 of the drill bit, for example less than 20% smaller or 1-20% smaller compared to cross-sectional diameter of the upper portion 324 of the drill bit 304 or wherein the cross-sectional diameter 396 upper part 324 of the drill bit 304 is 0.5-3 cm or 0.7-1.5 cm and the cross sectional diameter 212 for the upper part 234 of the guide channel is about 0.5-3 cm or 0.7-1.5 cm and the cross sectional diameter 262 inner part 232 of the guide channel 200 is 0.5-3 cm or 0.5-1 cm.

d. Generating design parameters for the cartilage repair objects 600 comprises generating design parameters for a cartilage repair objects 600 and also generating design for their placement relative to each other with a shortest distance 804 between the plugs or implants varying between 1-3 cm in diameter.

e. Generating design parameters for the positioning body 202 comprises generating design parameters for the cartilage contact surface 208 of the positioning body 202 having three contacting points 222, spread out around the guide body 206, for contacting parts of the joint in order to provide stable positioning of the guide tool 1 in the joint.

f. Generating design parameters for one or two guide channels 200 to have a height 218 of 0.3-20 cm or 3-10 cm.

The invention claimed is:

1. A method of designing a guide tool for cartilage repair in an articulating surface of a joint wherein the guide tool is provided with guide channels intended for insertion of cartilage and bone plugs and also for enabling of guiding insert tools, comprising the steps of:
   I. determining physical parameters for cartilage damage in a joint and generating design parameters for cartilage and bone plugs and their relative placement in a predetermined pattern, comprising:
   II. selecting repair objects to fit the individual cartilage damage site wherein the cartilage and bone plugs have surfaces intended to align with the articular cartilage surface in the joint, based on the healthy surface contour curvature;
   III. determining, based on obtained image data, positions and angles of the selected cartilage and bone plugs, wherein the positions and angles are adapted so that the selected cartilage and bone plugs fit the individual cartilage damage site, wherein said angle of said cartilage and bone plug is selected between 0-40 degrees in relation to the normal of a tangential plane drawn at a point at the articulate surface of the cartilage or of the bone where the axis of the guide channels intersect the articulate surface;
   IV. generating design parameters of the guide tool, for placement of the cartilage and bone plugs comprising the following steps;
   V. generating the design for an upper part and a lower part of a guide channel in a guide body extending from the positioning body, said guide channel passing through said positioning body and said guide body wherein the angles and positions are generated dependent on and substantially corresponding to the determined angles and positions of the selected cartilage and bone plugs and are selected between 0-40 degrees in relation to the normal of a tangential plane drawn at a point at the articulate surface of the cartilage or of the bone where the axis of the channels intersect the articulate surface, and wherein the design of each guide channel is provided with a stop function to delimit penetration by a cartilage and bone harvesting and insertion tool and to delimit bone drilling penetration by a drill bit at a site of cartilage damage, and is generated dependent on and substantially corresponding to the determined cross sectional areas, of the selected cartilage and bone plugs.

2. The method for designing a guide tool according to claim 1, wherein design parameters are generated for the guide channel to have a height of 0.3-20 cm.

3. The method for designing a guide tool of claim 1 wherein the cartilage and bone plugs are selected to fit the individual cartilage wherein the cartilage and bone plugs have:
   cross sectional areas adapted to fit the surface area of the cartilage damage site; and
   lengths adapted to fit the selected joint and/or type of cartilage damage or longer.

4. The method for designing a guide tool according to claim 1, wherein the cartilage and bone plug is a healthy cartilage and bone plug.

5. The method for designing a guide tool according to claim 1, wherein the cartilage contact surface may be 10-90% larger than the area of muzzles of the guide channels 200.

6. The method for designing a guide tool according to claim 1, wherein each cartilage and bone plug has a size of between 0.1 $cm^2$ and 5 $cm^2$.

7. The method for designing a guide tool according to claim 1, wherein the guide tool is intended to repair cartilage damage of areas between 0.1-10 $cm^2$ which is between 0.1-50% of the total cartilage area in a joint.

8. The method for designing a guide tool according to claim 1, wherein the guide tool is designed to repair cartilage damage of a size that is 1-70% of the total cartilage in the joint with high precision.

9. The method for designing a guide tool according to claim 1 wherein guide channels are designed to be oriented such that the longitudinal axis of the guide channel is inclined at a selected angle between 0-40 degrees in relation to the normal of a tangential plane drawn at a point at the articulate surface of the cartilage or of the bone where the axis of the channels intersect the articulate surface and in this way providing a desired and exact repair of the cartilage damage site.

10. The method for designing a guide tool according to claim 1 wherein said guide further is designed to comprise a hollow space which enables output of waste such as cartilage tissue and bone chips from boring or reaming in the preparation of the recess for the implant in the joint and/or also designed so that the surgeon easier can see the cartilage damage site.

11. The method for designing a guide tool according to claim 1 wherein the guide tool comprises a positioning body which extends laterally outside the periphery of the guide channel.

12. The method for designing a guide tool of claim 1, wherein image data representing an image of the joint is obtained using magnetic resonance imaging (MRI), computerized tomography (CT) imaging or a combination of both, or other suitable techniques such as delayed Gadolinium-enhanced MRI of cartilage (dGEMRIC) techniques or combinations of CT or MR and radio contrast agents.

13. A surgical method comprising the steps of:
a) using the data and the guide tool designed according to the design method described in claim 1;
b) mounting the individually shaped guide tool from step a) on the cartilage damage site and optionally fastening the guide tool to the cartilage;
c) using selected guide channels in the guide tool for guidance when drilling out recesses in the bone and cartilage within the cartilage damage site of the patient;
d) placing selected cartilage repair objects into recesses created in step c) using the guide tool for guidance.

14. A manufacturing method of the guide tool designed according to claim 1, wherein the manufacturing steps are dependent on the following factors:
the size of the cartilage and bone plugs needed;
the localization of the injury;
the appearance of the cartilage surface and/or bone intended to be replaced;
the placement of the cartilage and bone plugs in relation to the injury site and also in relation to each other and in a certain angle and depth; and the harvesting site such as non bearing cartilage in a joint wherefrom the healthy cartilage and bone plugs are harvested, wherein the insert tools are manufactured depending on the selected choices for the guide tool and also depending on the selected sizes for the healthy cartilage and bone plugs, wherein the designs may be based on the MR images/CT-scanning images from the joint of the person having the cartilage damage, using surgical planning software, and wherein the surgical planning software is connected to manufacturing devices, for example a laser printer, a lathe and/or a reamer, and the parts of the kit are manufactured using for example additive manufacturing, laser sintering techniques, turnery or reaming.

15. A method for designing a guide tool according to claim 1, wherein the relative shortest distances between the designed guide channels are 1-3 mm.

* * * * *